United States Patent [19]

Scallen et al.

[11] Patent Number: 5,783,594
[45] Date of Patent: Jul. 21, 1998

[54] CELL DIFFERENTIATION INDUCTION WITH MEVALONATE AND MEVALONOLACTONE DERIVATIVES

[75] Inventors: Terence J. Scallen; Paul L. Mann, both of Albuquerque, N. Mex.

[73] Assignee: University of New Mexico, Albuquerque, N. Mex.

[21] Appl. No.: 456,116

[22] Filed: May 31, 1995

Related U.S. Application Data

[63] Continuation of Ser. No. 314,457, Sep. 28, 1994, abandoned, which is a continuation of Ser. No. 786,215, Oct. 31, 1991, abandoned, which is a continuation-in-part of Ser. No. 694,284, May 1, 1991, abandoned.

[51] Int. Cl.$^6$ ................................................ A61K 31/415
[52] U.S. Cl. ............................................ 514/400; 514/415
[58] Field of Search ................................... 514/400, 415

[56] References Cited

U.S. PATENT DOCUMENTS

| 4,613,610 | 9/1986 | Warung ................... 514/406 |
| 4,808,607 | 2/1989 | Warung ................... 514/400 |
| 4,933,185 | 6/1990 | Brown . | |
| 4,970,221 | 11/1990 | Magnin et al. . | |

FOREIGN PATENT DOCUMENTS

| 0 401 784 | 12/1990 | European Pat. Off. . |
| 0 428 094 | 5/1991 | European Pat. Off. . |
| WO 92/19105 | 11/1992 | WIPO . |

OTHER PUBLICATIONS

Mann, "Membrane Oligosaccharides: Structure and Function during Differentiation", International Review of Cytology 112:67–96 (1988).

*Primary Examiner*—Rebecca Cook
*Attorney, Agent, or Firm*—Nixon & Vanderhye P.C.

[57] ABSTRACT

The invention provides cell modulators comprising certain biologically-active enantiomers of mevalonate and mevalonolactone derivatives. The compounds are broadly clinically useful, particularly in cancer management and treatment of immunological diseases or disorders.

5 Claims, 9 Drawing Sheets

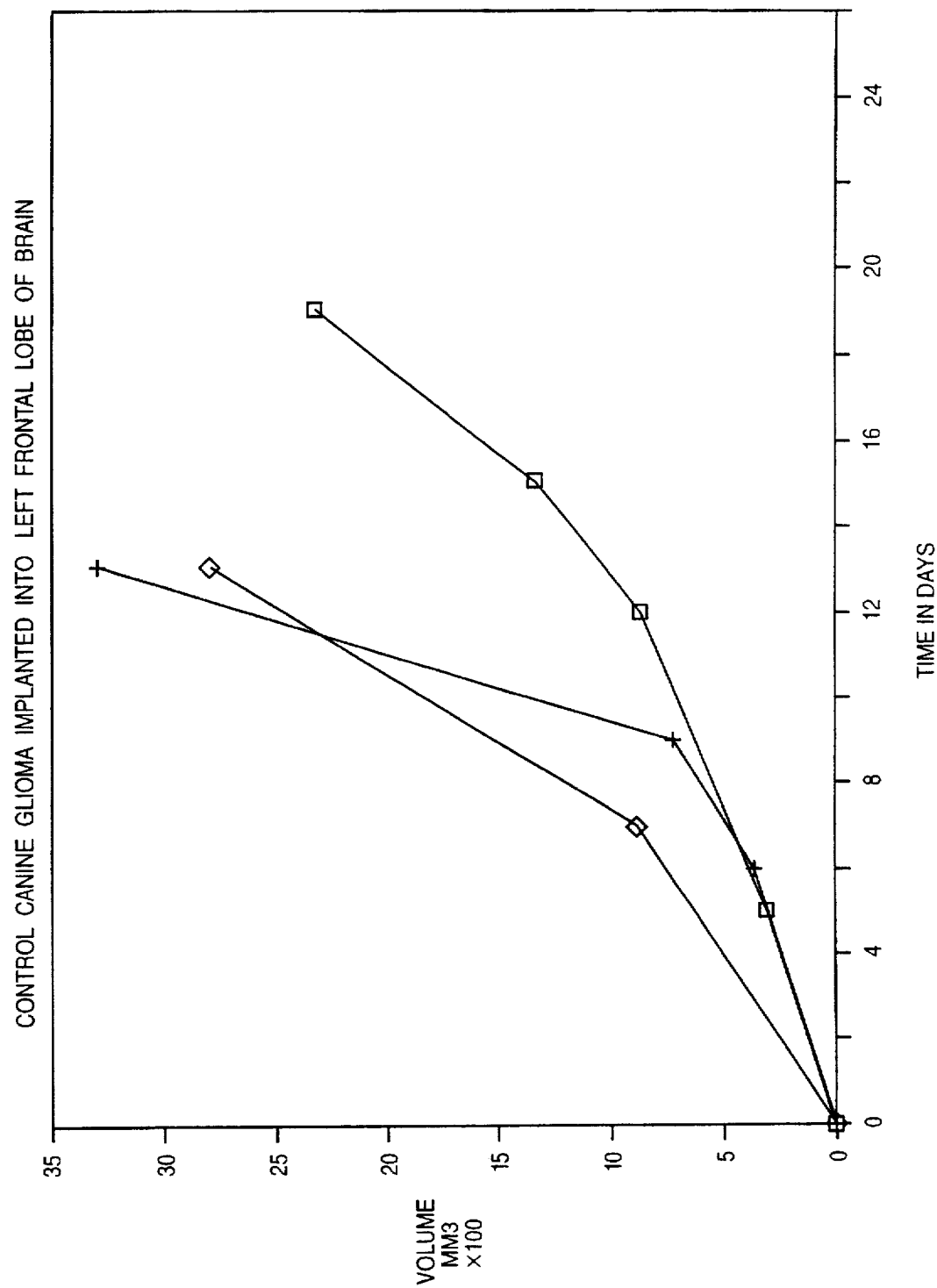

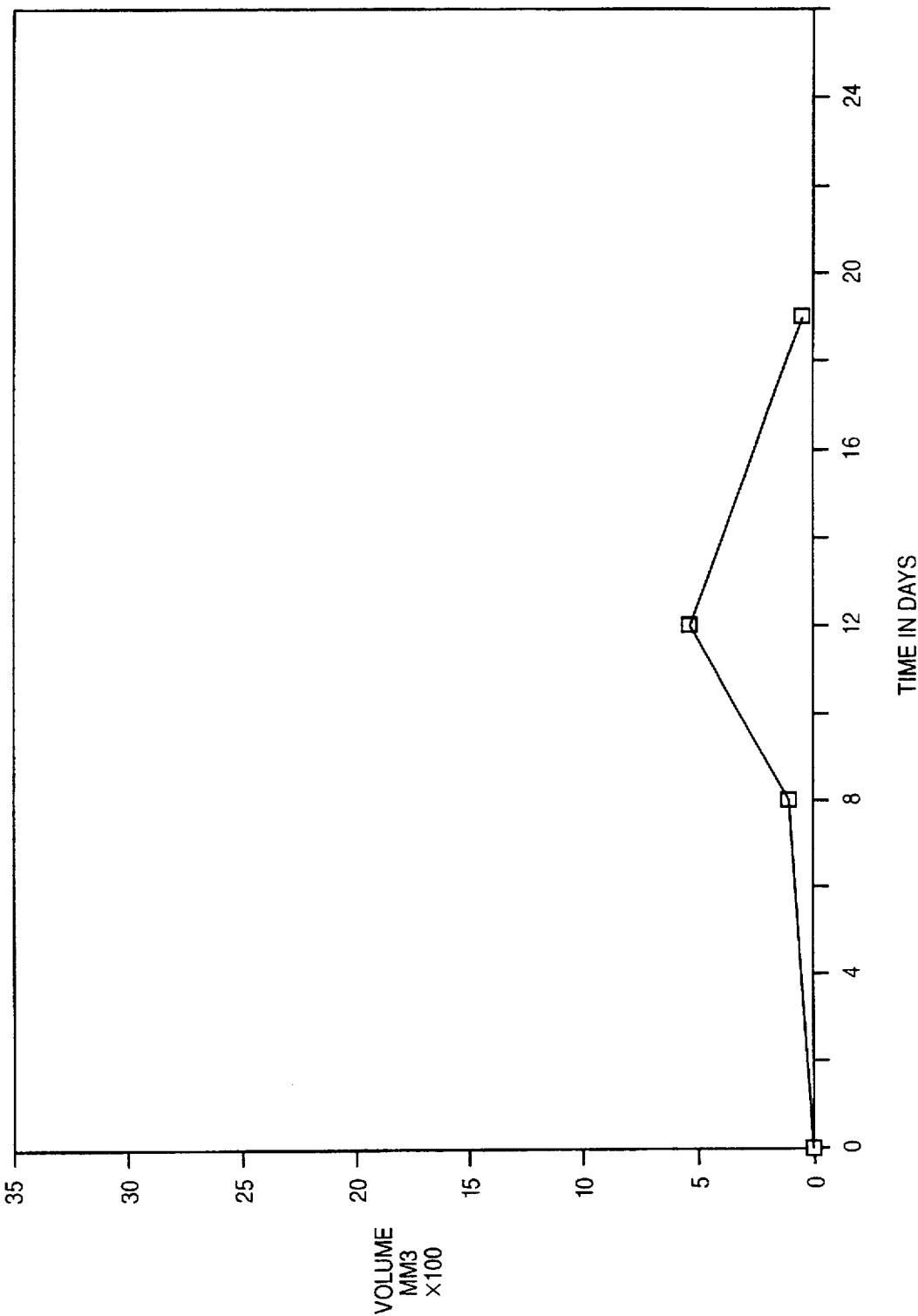

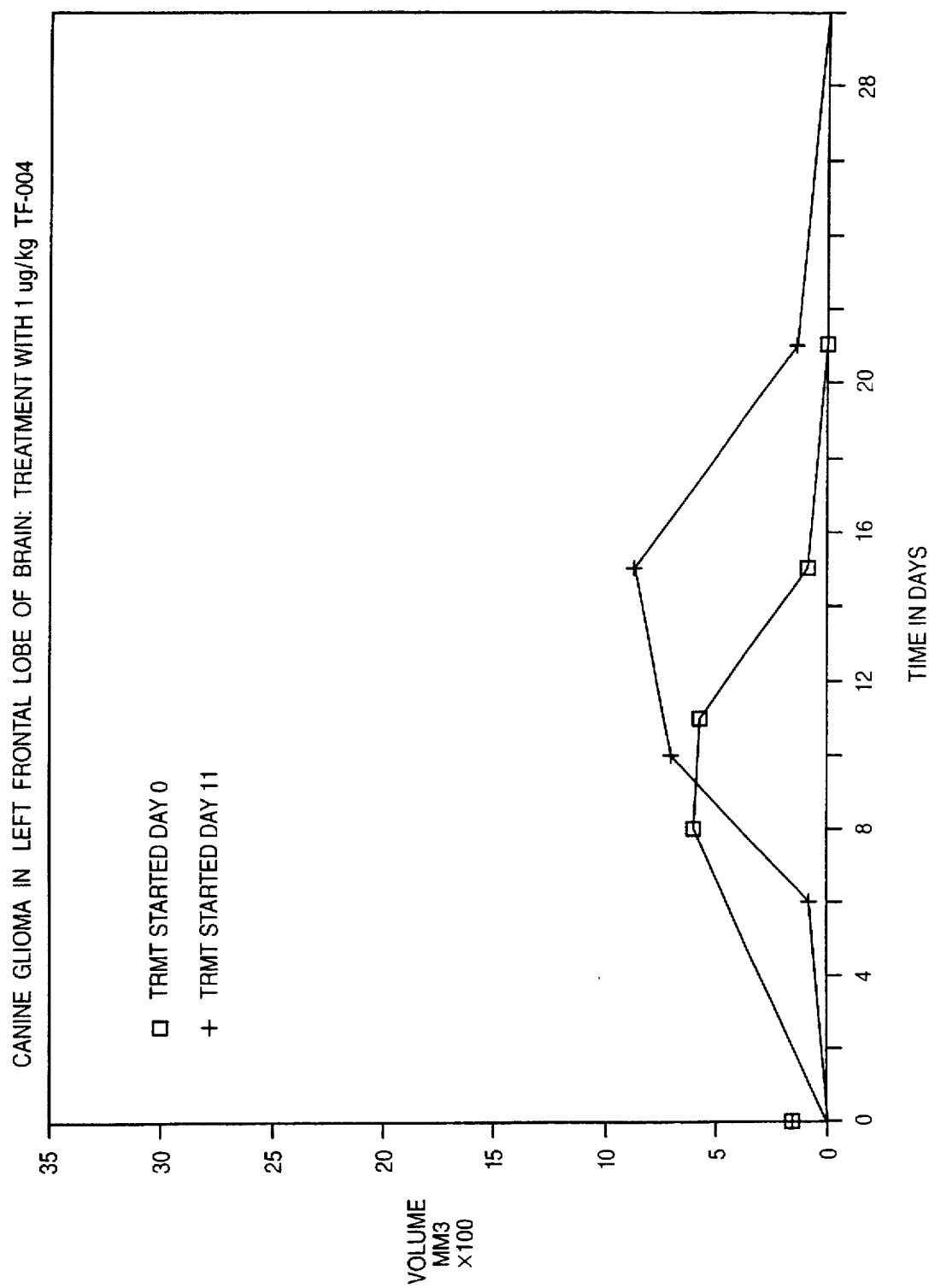

CELL DIFFERENTIATION INDUCTION WITH MEVALONATE AND MEVALONOLACTONE DERIVATIVES

This is a continuation of application Ser. No. 08/314,457, filed Sep. 28, 1994, abandoned which is a cont. of Ser. No. 07/786,215, filed Oct. 31, 1991; abandoned which is a CIP of 07/694,284, filed May 1, 1991, abandoned.

GOVERNMENT RIGHTS

Research leading to this invention was at least partially funded by the United States Government, NIH Grant HL-16, 796-13, and the Government accordingly may have substantive statutory rights in this patent.

BACKGROUND OF THE INVENTION

1. Field of the Invention

The invention relates to cell function modulators particularly useful as immunomodulators for treatment of immune disorders or diseases or as cytostatic agents for cancer management.

2. Discussion of Related Art

Cell activity is broadly divisible into two general categories: proliferation (reproduction) and differentiation (individualized function). According to present theory, proliferative function is continuously present in the normal cell, and is dominated in the mature cell by the differentiative function, which thus acts as an integrative force to regulate both differentiative and proliferative activity in the individuated mature cell. A failure in the biochemical mechanisms upon which the mature cell is dependent for control of cell differentiative activity thus has important implications, as disruption of normal differentiative controls may accordingly result in both abnormal cell function and abnormal cell growth patterns.

The possibility of regulating cell behavior by the use of factors which independently regulate cell growth or differentiation has been previously presented. The identification of factors which induce cell differentiation has been of particular interest, because such factors are potentially capable of inducing maximum cellular gene expression, coding for cell functions and structures characteristic of the normal mature cell, with, for example, increased production of cell products of commercial interest.

The recognition of these cellular phenomena has led to the postulation of a variety of mechanisms by which cell activity is controlled in vivo and by which cell activity may be manipulated. For example, in a recent publication, (Sachs, Sci. Am. Vol. 254, pp. 40–47, January 1986, incorporated herein by reference), it is reported that each cell produces its own differentiation factors in response to endogenous "growth factors" which function as growth inducers for the cell. As the cells multiply under the influence of these "growth factors", concentrations of cell differentiation factor produced by the growing cells increase sufficiently to induce cell differentiation. Sachs concludes that these cell-produced differentiation factors are specialized proteins, probably as numerous as the cell types whose maturation they induce. The publication also reports that compounds other than cell-produced differentiation factors may directly or indirectly induce differentiation in normal and genetically defective cells in vivo, such as steroid hormones, X-rays, vitamins, bacterial lipopolysaccharide, cytosine arabinoside, adriamycin, methotrexate, lectins, and some phorbol esters. No one compound appeared to effectively induce all differentiation over the broad range of cells tested.

These phenomena are additionally explored in "In Vitro Differentiation of Human Peripheral Blood Leukocytes: Considerations for Monoclonal Antibodies", (Mann, in Radioimmunoimaging and Radiotherapy, pp. 121–141, Elsevier Science Publishing Co., Inc., Eds. Burchiel and Rhodes, 1983, incorporated herein by reference), with particular reference to the induction of functionally differentiating cells with limited proliferative capacity. In vivo induction of differentiation in leukocytes with fractionated pokeweed mitogen, anti-immunoglobulin, and lipopolysaccharide, followed by exposure to antigen, produced particularly good antibody responses over an extended culture life. The publication emphasizes the dual role of pokeweed mitogen as inducer: at proliferative concentrations of the mitogen, leukocyte antibody production is stimulated in vitro by inducing proliferation of the cells; under this stimulation, however, the cells rapidly age and prematurely die. In contrast, at differentiative concentrations of the same mitogen, long-term cultures of differentiated cells producing antigen-specific immunoglobulins at stabilized levels are obtained.

Research on factors potentially useful for regulating or modulating cell activity in vitro or in vivo extending over half a century has identified a large number of compounds erratically effective in differentiating a very narrow range of cell types under carefully controlled conditions. The unpredictable end utility of these compounds may be attributable to the complexity of the poorly-understood pathways by which cell proliferation and differentiation are regulated, the unpredictable point at which these prior art compounds intervene in these pathways, and the consequently substantially random effects of these compounds on the basic underlying mechanisms controlling differentiation and proliferation.

It is accordingly desirable to provide compounds which directly affect the primitive control mechanisms regulating differentiation of cells, to which cells can be exposed in vivo or in vitro to obtain a predictable alteration in cell differentiative activity over a broad range of cell types. In particular, it is desirable to provide compounds which can induce self-adjustment of pathological cell behavior to return pathological cells to normal function wherein reproductive and differentiative cell activities are integrated and responsive to the requirements of the host organism.

BRIEF DESCRIPTION OF THE DRAWING

FIGS. 7–9 graphically illustrate tumor response (canine glioma cells implanted in dogs) in two compounds according to the invention (FIGS. 8 and 9), as compared to tumor growth in control dogs (FIG. 7).

SUMMARY OF THE INVENTION

Figure 1:
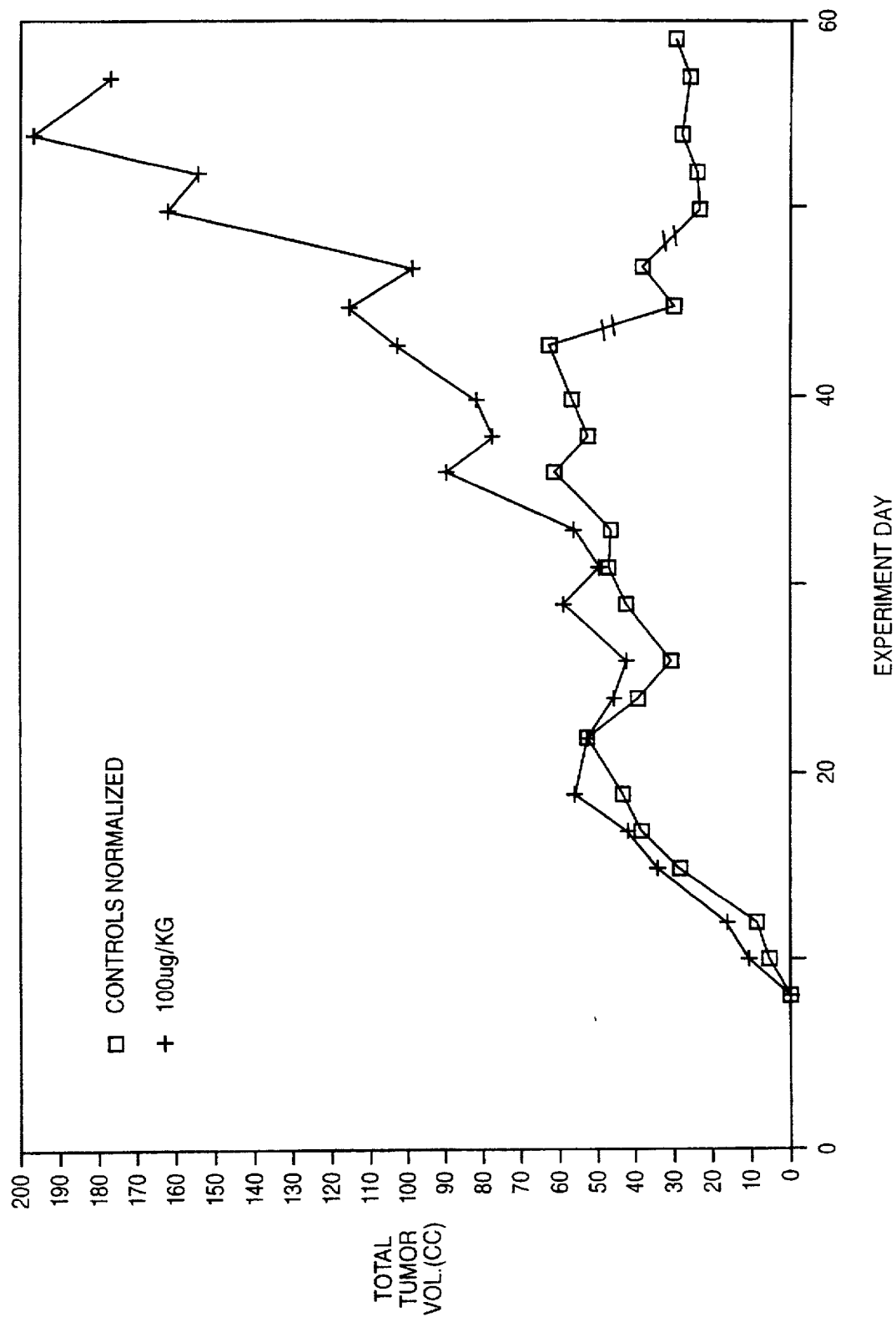
FIGS. 1–6 graphically illustrate tumor response (canine glioma cells implanted in nude rats) to varying dosages of a compound according to the invention.
Figure 2:
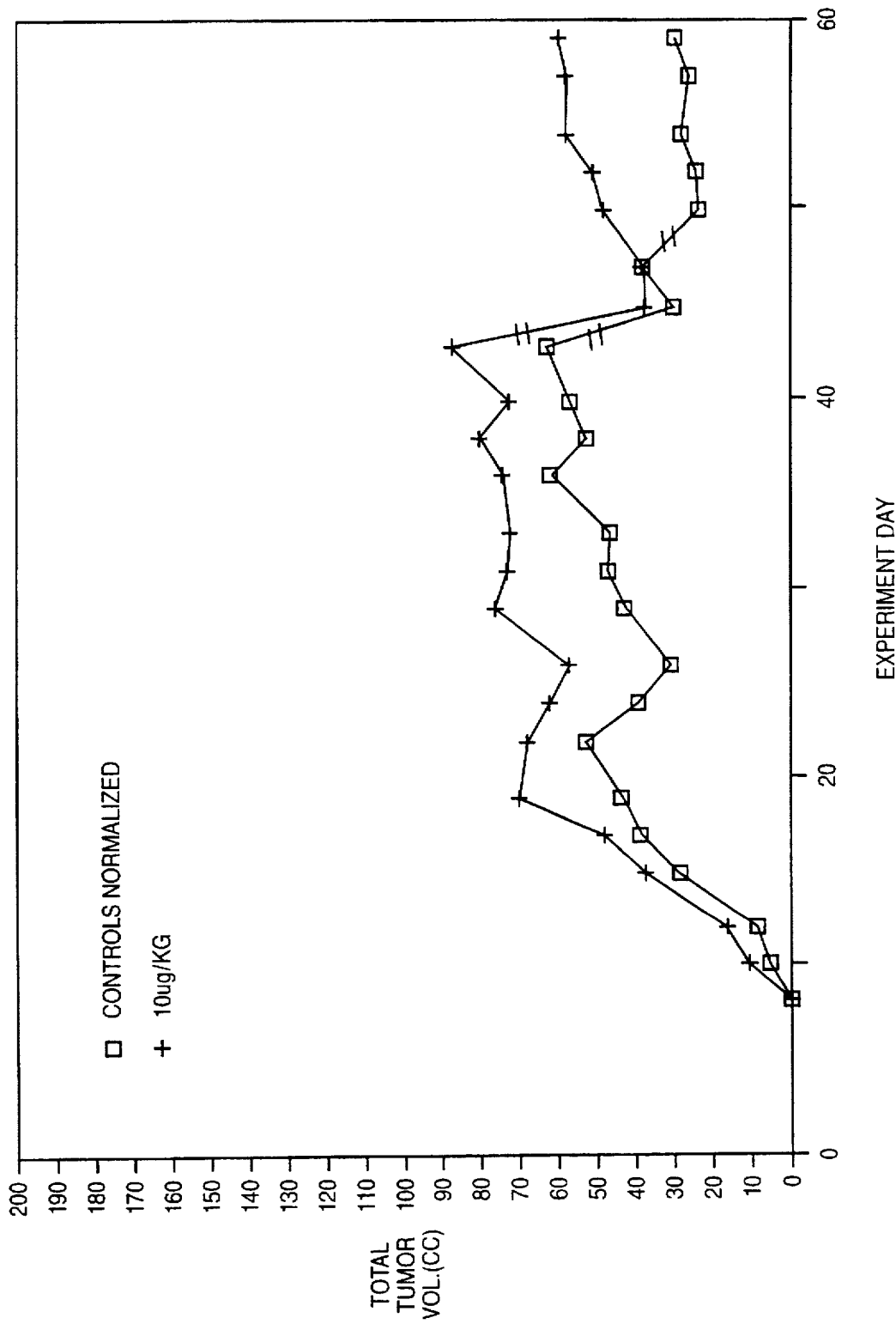

The present invention provides modulators comprising biologically-active mevalonic acid and mevalonolactone derivatives defined by a specified steric configuration which promote autoregulation of abnormal cell differentiative function to restore the genetically sufficient (genetically non-defective) cell to normal differentiative and proliferative behavior, and which include diversification of cell differentiative function within the genetic potential of the cell. Thus, the compounds are useful for normalizing pathological cell function of genetically-sufficient cells to restore the cell to normal behavior, particularly normal proliferative and immunological function.

The modulators appear to obtain their effect of differentiation by modulating expression of the cell differentiative phenotype; inter alia, the modulators appear to induce expression of unexpressed genes to significantly diversify cell function, or to induce significant increase in an existing cell function. The modulators further counteract abnormal proliferative or differentiative cell function in genetically-sufficient cells by stimulating intracellular biochemical controls to normalize cell behavior.

The modulators of the invention produce their results in very low concentrations and are characterized by a low molecular weight, generic intervention properties, high specificity, and controllable end-point response. The compounds are nontoxic in the amounts employed in the process of the invention. It is theorized that the modulators simulate or comprise mechanisms controlling cell differentiative behavior and/or integration of cell proliferation and differentiation activity on a primitive level, thus accounting for the applicability to a broad range of processes.

The compounds are clinically useful, for example, in the treatment of pathological cell function, particularly in therapeutically effective amounts as cytostatic agents for inhibiting growth of tumor cells and/or inhibiting tumor metastasis. The compounds are broadly capable of inhibiting increases in tumor burden in a host, and/or are also capable of reducing pre-existing tumor burden. Therapeutically effective amounts of the compounds are further particularly clinically immunologically useful in treatment of immune diseases or disorders, such as acquired immune deficiency syndrome (AIDS) and autoimmune disorders such as rheumatoid arthritis, lupus erythematosus, hypogammaglobulinemia, and juvenile diabetes.

DETAILED DESCRIPTION OF THE INVENTION

A. The Compounds

The compounds of the invention comprise mevalonate and mevalonolactone derivatives or the Formula I:

$$A—X—Z \quad (I)$$

wherein

X is a direct bond, $C_1$-$C_3$-alkylene or $C_2$-$C_3$-alkenylene;

Z is

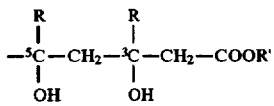

or the corresponding lactone,

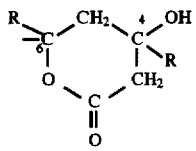

each R is independently H, $C_1$-$C_3$-alkyl, or another physiologically-acceptable substituent; R' is hydrogen, a physiologically-acceptable cation or cation complex M, or a physiologically-acceptable ester group $R_2$; and A is a physiologically-acceptable substituent, characterized by a substituted or unsubstituted ring system containing at least one aromatic, cycloaliphatic or heterocyclic ring; with the proviso that the compounds or the Formula I;

a) are biologically-active as defined below; and b) have a steric configuration as described below.

As used herein, the term "mevalonate" includes free mevalonic acid, its esters and its salts as defined above for R'.

Compounds within the scope of Formula I are those which have a stearic configuration at the designated 3,5- or 4,6-carbon atoms of the mevalonate or mevalonolactone radical Z as described below.

The expression "physiologically-acceptable" modifying the definitions of the groups A, R, R', M, and $R_2$ refers to groups which are nontoxic at the accepted dosage levels and which do not substantially decrease the cytostatic activity of the compounds attributable to the character of the —X—Z moiety. In the case of the ester group $R_2$ or the salt group M, the term "physiologically-acceptable" further refers to groups $R_2$ or M which are hydrolyzable under physiological conditions to yield the corresponding biologically-active carboxyl anion and a substantially nontoxic by-product. Preferably, the substituents A, R, R', M and $R_2$ are free from centers of asymmetry. It is believed the substituent A functions to bind the compounds to specific hydrophobic sites in proteins essential for cell differentiation or regulation and does not per se contribute to the active properties of the compounds.

Suitable radicals A, X, R, and R' in the Formula I include the following:

X is methylene, ethylene, propylene, ethenylene, 1-propenylene, or 2-propenylene;

R is hydrogen or methyl;

R' is a monovalent cation or cationic complex M such as sodium, potassium or ammonium; or a di- or trivalent cation or cationic complex such as magnesium or calcium, particularly wherein A—X—Z is a compound of the Formula A and x is 2 or 3:

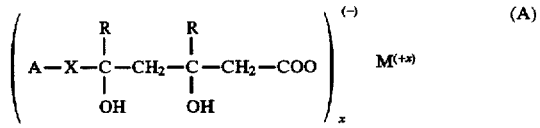

or R' is an esterifying group $R_2$ such as benzyl; or branched or unbranched $C_{1-4}$-alkyl such as $C_{1-3}$-alkyl, especially methyl or ethyl;

A is substituted or unsubstituted mononuclear -aryl or -aryloxy; polynuclear -aryl or -aryloxy; binuclear -aryl or -aryloxy; alkaryl or alkaryloxy; cycloalkyl; cycloalkenyl; or heterocyclyl; such as benzyl; benzyloxy; phenyl; phenyloxy; naphthyl; naphthyloxy; tetrahydronaphthyl; imidazolyl; pyrimidyl; pyrazolyl; indenyl; quinolinyl; pyrrolyl; indolyl; azaindolyl; indolizinyl; $C_4$-$C_6$-heterocyclyl wherein the heteroatom is O, S, or N, especially wherein the ring system contains at least one double bond; $C_4$-$C_6$-cycloalkyl or -cycloalkenyl;

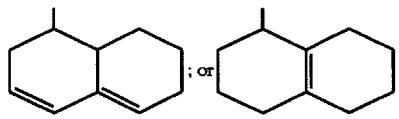

Exemplary compounds are described in the following patents, each of which is incorporated herein by reference: U.S. Pat. No. 4,755,606, issued to Wareing Jul. 5, 1988; U.S. Pat. No. 4,613,610, issued to Wareing Sep. 23, 1986; U.S. Pat. No. 4,255,444, issued to Oka et al Mar. 10, 1981; U.S.

Pat. No. 4,248,889, issued to Oka et al Feb. 3, 1981; U.S. Pat. No. 4,761,419, issued to Picard et al Aug. 2, 1988; U.S. Pat. No. 4,751,235, issued to Anderson Jun. 14, 1988; WO 84/02903, published Aug. 2, 1984; WO 87/02662, published May 7, 1987; WO 88/01997, published Mar. 24, 1988; WO 86/03488, published Jun. 19, 1986; U.S. Pat. No. 4,198,425, issued to Mitsui et al Apr. 15, 1980; U.S. Pat. No. 4,137,322, issued to Endo et al Jan. 30, 1979; U.S. Pat. No. 3,983,140, issued to Endo et al Sep. 28, 1976; U.S. Pat. No. 4,588,715, issued to Damon May 13, 1986; U.S. Pat. No. 4,710,513, issued to Willard et al Dec. 1, 1987; U.S. Pat. No. 4,739,073, issued to Kathawala Apr. 19, 1988; and U.S. Pat. No. 4,681,893, issued to Roth Jul. 21, 1987.

The compounds described in these publications which have the appropriate stereochemistry at the 3,5 carbon atoms of their mevalonate Z moieties or 4,6 carbon atoms of their mevalonolactone moieties Z as defined below are contemplated as useful in the process of the present invention as inducers of cell differentiation, particularly for reducing tumor burden or for treating immune diseases or disorders. Preferred compounds are those which exhibit positive in vitro immunological activity, as defined below, and particularly concomitant cytostatic activity.

B. Compound Activity

Compounds of the Formula I useful in the process of the invention comprise those compounds which are capable of modulating cell differentiation activity as described above. Particular compounds having modulating activity include compounds having cytostatic activity against tumor-transformed cells which are effective in therapeutic dosages according to the invention to reduce tumor burden in vivo by inhibiting primary or secondary tumor cell growth, or tumor metastasis, or both. A broad spectrum of tumors are contemplated as susceptible to treatment according to the invention including both soft tumors such as leukemias and lymphomas; and solid tumors such as melanomas; ovarian tumors; cervical tumors; breast tumors; lung tumors (small cell and non-small cell); colon and stomach tumors; hepatocellular tumors; pancreas, midgut bladder, and prostate tumors; brain tumors; myelomas, and larynx tumors.

Compounds within the scope of Formula I having cytostatic activity within the scope of the present invention are conveniently selected by assaying immunological activity in vitro, as this property appears to be a marker of cytostatic activity; in some instances, however, compounds within the scope of the invention having little or no immunologic activity may also be cytostatically active. Numerous in vitro assays for immunological activity are available to those skilled in the art; an exemplary in vitro assay for immunological activity suitable for selecting compounds of the Formula I having the capability to modulate cell differentiation for use in the process of the present invention is hereinafter described (Example II).

As defined herein, "immunologically-active compounds" within the scope of Formula I comprise those compounds which enhance host immune system function by inducing either humoral or cellular based immunity. Of special interest are compounds which enhance the cellular immune system, in particular the immune response of natural killer (NK) cells, which are generally currently recognized as a primary line of defense against endogenous tumor-transformed cells, particularly solid tumor cells.

A convenient in vivo test for establishing positive cellular immunological activity is set forth in Example III2, wherein it is demonstrated that compounds within the scope of Formula I which have a stimulatory effect on the cellular immune system also have a particularly effective cytostatic effect according to the invention against tumor-transformed cells.

Immunologically-active compounds within the scope of the invention also include compounds exhibiting immunological enhancement of the humoral immune system. Preferred compounds of the Formula I for anti-tumor applications comprise immunologically-active compounds capable of increasing in vivo production of immunoglobulin fractions, especially IgG, containing antibodies specific to antigenic determinants borne by host tumor cells. Convenient in vitro and in vivo assays for establishing humoral immunoactivity are described in the Examples. Preferred compounds according to the invention as cytostatic agents are those exhibiting capacity for boosting either cellular or humoral immune response to established tumors, or both.

While a number of the compounds of the Formula I are known HMG-CoA reductase inhibitors, there is no apparent correlation between HMG-CoA reductase inhibitory activity and promotion of differentiation activity according to the invention. For example, compounds within the scope of Formula I having high activity as HMG-CoA reductase inhibitors are not necessarily effective inducers of differentiation according to the invention; conversely, compounds exhibiting little or no HMG-CoA reductase inhibitory activity may be excellent inducers of cellular differentiation. The invention is predicated in part on the discovery that compounds exhibiting even little or no significant HMG-CoA reductase inhibitory activity, as evaluated, for example, by the in vitro test described in *J. Biol. Chem.* 234:2835(1959) are useful differentiating compounds, particularly cytostatic agents and immunomodulators according to the invention if, in addition, these compounds further enhance immune system response, for example, to tumor-specific antigens, or to viruses or virus-transformed cells. Accordingly, useful guidelines for selecting compounds having optimal differentiation-promoting activity according to the invention broadly comprise selecting compounds of the Formula I having the specified stereochemical configuration and an in vitro immunological activity as set forth in the in vitro assay of Example II, of at least about 3-fold.

In theory, it is believed that the cytostatic modulators of the invention function at least in part to normalize cell-surface membrane characteristics and restore normal cellular mechanisms controlling cell growth. In particular, there is evidence that the modulators of the invention employed as cytostatic agents tend to re-establish normal cell-surface oligosaccharide display associated with contact inhibition mechanisms which restrain growth of normal (non-transformed) cells. An elaboration of the correlation of high-affinity lectin binding sites with normal cell growth is provided in *Int. Rev. Cytol* 112:67–96(1985), incorporated herein by reference; the compounds of the present invention may modify tumor cell-surface oligosaccharides to restore high-affinity sites and normal growth control mechanisms in tumor-transformed cells. This concept is in part based on the observation (see e.g., Example V) that cells of tumors treated according to the invention evidence an increase of the generation time and signs of normalized contact inhibition.

C. Compound stereochemistry

As described in the patents cited above, for example, U.S. Pat. No. 4,613,610, the compounds of the Formula I each contain two asymmetric carbon atoms, comprising the 3 and 5 carbon atoms of the mevalonate derivatives and the 4 and 6 carbon atoms of the mevalonolactone derivatives; when no additional asymmetric carbons are present in the molecule, each compound of the Formula I thus encompasses four stereoisomers (enantiomers) generally designated as R,R; R,S; S,R; and S,S enantiomers. Two of the four mevalonate derivative enantiomers have the erythro (syn) configuration and the other two have the threo (anti) configuration, and two of the four mevalonolactone derivative enantiomers have the cis configuration and the other two have the trans configuration. The conventions employed to characterize the enantiomers useful in the present invention and their racemic mixtures are those commonly used in the art, and are explained in detail in U.S. Pat. No. 4,613,610.

As described below, certain of the enantiomers within the scope of Formula I which do not have the specified steric configuration are substantially inactive in the process of the present invention, and the invention is directed to the use of differentiatively-active enantiomers. Separation of mixtures of the enantiomers to remove inactive species is accordingly recommended; this is readily accomplished by conventional procedures,as described, for example, in U.S. Pat. No. 4,613,610. Alternatively and preferably, the desired differentiatively-active enantiomers are synthesized by processes that yield only or substantially only the desired enantiomers. Such processes are well known in the art. However, the presence of contaminating inactive species in therapeutic compositions for use according to the invention is not generally detrimental, with the caveat that the presence of any inactive compounds must be considered in calculating therapeutic dosages,and the use of immunosuppressive enantiomers is not recommended. Accordingly, the invention also includes racemic mixtures of each of the active enantiomers of the invention.

Biologically-active enantiomers of compounds of the Formula I useful in the process of the present invention comprise the R,R; S,S, and S,R enantiomers of mevalonate and their racemic mixtures when the terminal carbon atom of the bridging moiety X linking X to Z is unsaturated or X is a direct bond, and comprise the R,R; S,S; and R,S enantiomers of mevalonate and their racemic mixtures when the terminal carbon atom of the bridging moiety X linking X to Z is saturated.

Thus, for example, when —X—Z is —Z, —CH=CH— Z, or —CH$_2$—CH=CH—Z, biologically-active enantiomers according to the present invention comprise the 3R,5R; 3S,5S; and 3S,5R enantiomers and the corresponding 3R,5R-3S,5S and 3R,5S-3S,5R racemates thereof when Z is a mevalonic acid, ester, or salt moiety and comprise the 4R,6R; 4S,6S; and 4S,6R enantiomers and the corresponding 4R,6R-4S,6S and 4R,6S-4S,6R racemates thereof when Z is a mevalonolactone moiety. Conversely, when —X—Z is —(CH$_2$)$_m$—Z(m>0) or —CH=CH —CH$_2$—Z and Z is a mevalonic acid, ester, or salt moiety, biologically-active enantiomers according to the present invention comprise the 3S,5S; 3R,5R; and 3R,5S enantiomers and their corresponding 3S,5S-3R,5R and 3S,5R-3R,5S racemates, and comprise the 4S,6S; 4R,6R; and 4R,6S enantiomers and the corresponding 4S,6S-4R,6R and 4S,6R-4R,6S racemates when Z is a mevalonolactone moiety.

In summary, compounds useful in the process of the present invention broadly comprise biologically-active enantiomers of compounds according to the Formula I, including mixtures thereof. The differentiators of the invention more particularly comprise compounds of the Formula I, including enantiomers thereof and their corresponding racemates, with the proviso that when X is a direct bond or contains a terminal unsaturated carbon atom linking X to Z, neither the 3R,5S (mevalonate) nor the 4R,6S (mevalonolactone) enantiomer is included and that when X contains a terminal saturated carbon atom linking X to Z, neither the 3S,5R (mevalonate) or 4S,6R (mevalonolactone) enantiomer is included. As indicated above, and as further set forth below, the 3R,5S (4R,6S) and 3S,5R (4S,6R) enantiomers excluded by this proviso are substantially inactive in the therapeutic processes of the invention; moreover, it appears that these compounds may be characterized by undesirable immunosuppressive activity. Enantiomers of particular note in this latter category include compactin and lovastatin (mevinolin), as set forth in Examples II and Table I (no immune enhancement). Optimal differentiator activity of compounds of the Formula I, according to the invention, thus appears to be dependent upon the precise stereochemistry of the 3,5 or 4,6 carbon atoms of the radical Z (Formula I) and the character of the bridging radical X, and appears to be evidenced by immunological activity, as defined supra. It is thus contemplated that immunological activity, particularly stimulation of IgG antibody production, is predictive of differentiator activity, and particularly, cytostatic activity, of compounds of the Formula I having the specified stereochemistry at the 3,5 or 4,6 carbon atoms of the radical Z.

Particularly useful compounds according to the Formula I are compounds of the Formula II:

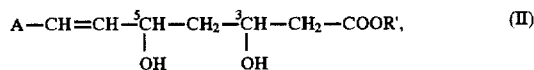

wherein A and R' are as defined for the Formula I. Differentiatively-active enantiomers of the Formula II include the following:

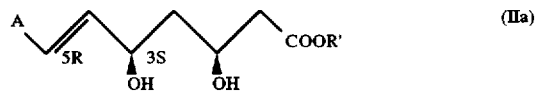

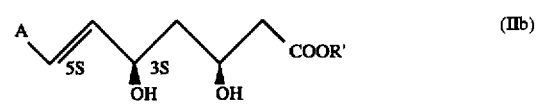

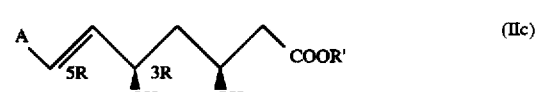

In the compounds of the Formulas I and II, A is, for example:

1) imidazolyl, especially

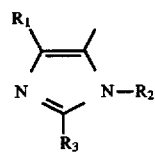

wherein R$_1$, R$_2$, and R$_3$ are as described in U.S. Pat. No. 4,755,606, especially

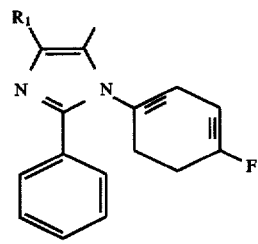

2) a compactin radical such as wherein R is defined in U.S. Pat. No. 3,983,140 and $R_1$ is H or $CH_3$;

3) pyrazolyl, especially wherein $R_1$–$R_7$ are defined in U.S. Pat. No. 4,613,610; or wherein $R_1$–$R_3$ are as defined in U.S. Pat. No. 4,751,229;

4) substituted or unsubstituted aryl or aryloxy such as exemplified in U.S. Pat. Nos. 4,248,889 and 4,255,444 and defined therein as "Z", especially phenyl, naphthyl or tetrahydronaphthyl substituted or unsubstituted with halo or $C_1$–$C_3$-alkyl or both, particularly chloro or methyl, or phenoxy or naphthoxy unsubstituted or substituted with halo;

5) indolizinyl or azoindolyl, especially wherein $R^1$ and $R^2$ are as defined in U.S. Pat. No. 4,751,235; and further especially wherein $Y^1$, $Y^2$, $Y^3$, $Y^4$, X, $X^1$, $R_{10}$, $R_{11}$, $R_2$ and $R_{14}$ are as defined in PCT application WO 88/01997, particularly wherein one Y is N, each of the others is CH, and $X^1$ is N; or each Y is CH, $X^1$ is $CR_1R_{15}$, and X is N;

6) pyrrolyl, especially wherein $R_1$–$R_4$ are as defined in U.S. Pat. No. 4,681,893;

7) quinolinyl, especially wherein $R_1$–$C_6$ are as defined in U.S. Pat. No. 4,761,419;

8) indolyl, especially wherein R, $R_2$, $R_3$, and $R_0$ are as defined in U.S. Pat. No. 4,739,073;

9) indenyl, especially wherein $R_0$, R, $R_1$, $R_2$ and $R_3$ are as defined in PCT application WO 86/03488;

10) $C_4$–$C_9$-heterocyclyl containing one or more heteroatoms, especially O, S, or N; unsubstituted or substituted, for example, with halo, especially chloro, bromo, or fluoro, $C_1$–$C_4$-alkyl, $C_1$–$C_4$-haloalkyl, $C_1$–$C_4$-alkoxy, phenyl, benzyl, phenyloxy, or benzyloxy; such as wherein Y is O, S, or N and $R_a$, $R_b$, $R_c$, and $R_d$ are as defined in PCT application WO 87/02662, and either $R_a$ or $R_b$ is a free valence;

11) phenyl, either substituted or unsubstituted, especially

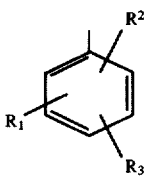

wherein $R_1$–$R_3$ are as defined in U.S. Pat. No. 4,710,513; or

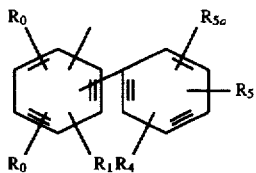

wherein $R_0$, $R_1$, R, $R_4$, $R_5$ and $R_{5a}$ are as defined in PCT application WO 84/02903; or

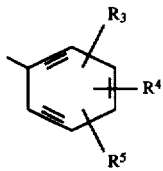

wherein $R^3$, $R^4$ and $R^5$ are as defined in U.S. Pat. No. 4,198,425; or

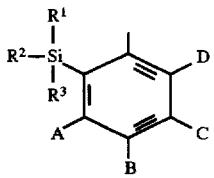

wherein A, B, C, D, $R^1$, $R^2$, and $R^3$ are as defined in U.S. Pat. No. 4,588,715.

Biologically-active compounds according to the invention also comprises the 4R,6R; 4S,6S; and 4S,6R enantioners and the racemates thereof of the lactones corresponding to the compounds of Formula II a–c.

Biologically-active compounds according to the invention particularly comprise enantiomers of the Formulas IIa–IIc wherein A is

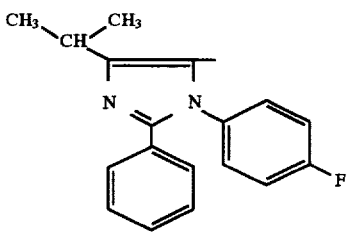

and racemic mixtures thereof.

Preferred compounds include compounds IIa', IIc' and TF004, as well as 3S,5R-colletruncoic acid and the compound obtained by switching the heptanoate chain of 3S,5R-colletruncoic acid with the adjacent methyl group on the ring.

D. Utility of the Compounds

According to the invention, cells which exhibit incompetent differentiative activity are exposed either in vivo or in vitro to a mevalonate or mevalonolactone modulator as described herein to improve cell differentiative activity, especially to rectify abnormal differentiative activity or to diversify cell differentiative activity. Within the scope of the present invention, "differentiative activity" refers to substantially all differentiative activities of the normal mature cell including bioproduction of cell proteins, carbohydrate and fats such as cholesterol and hormones, enzymes, sugars; immunoproducts such as globulins and antibodies; growth regulation functions which maintain or impose normal growth patterns; and cell structure regulation functions which provide cell structures characteristic of normal cell differentiative function, such as cell membrane composition, e.g., oligopolysaccharide structure, or cytoplasmic composition. Thus, the process of the invention provides a method for the autoregulation of cellular functions comprising virtually all functions characteristic of the mature individuated cell; i.e., those functions not peculiar to early progenitor cells having a purely proliferative capability, and further provides a method for increasing biologically adequate cell differentiative activity by inducing expression of unexpressed cell differentiative capacity, for example, to diversify expression of differentiative activity, or to induce differentiative activity in immature, substantially non-individuated cells, or in abnormally differentiated cells, e.g., transformed or aberrant cells.

The term "autoregulation" as used herein refers to the utility of the modulators in restoring cellular biochemical balance to cells exhibiting abnormal differentiative activity owing to known or unknown factors; such as toxic substances introduced into the organism from the environment; biochemical imbalance of the organism caused by metabolic disturbances, diseases, or disorders; or injury to the cell, organ, or organism. The term "autoregulation" further includes the utility of the modulators in the rectification of cell activity heretofore regarded as "normal", such as arresting senescence of cells both in vivo and in vitro, and diversification of cell function with respect to existing cell function within accepted ranges of normal cell function.

The differentiators of the invention accordingly function to stimulate phenotypic cell expression, including rectification of abnormal cell production, reassertion of normal cell function, correction of cellular incompetence, restoration of normal growth patterns, modulation of aberrant cell structures, reestablishment of normal cell growth patterns, and, further, diversification and/or expansion of existing cell function within the genetic capabilities of the cell.

The term "abnormal" as used herein to modify differentiative activity refers to cell differentiative activity as described above which is outside of accepted ranges; thus, "abnormal differentiative activity" refers to pathological cell differentiative activity manifested in cell morphology and/or activity above or below accepted standards, and which in vivo tends to result in malfunction of the organism resulting in distress, debilitation, and/or death of the organism.

Exposure of cells to the differentiators according to the invention invokes cell mechanisms which promote normal differentiative activity or which expand or diversify cell differentiative activity. In applications wherein the differentiators are employed to improve abnormal differentiative activity, at least a 10% improvement in such function is contemplated; i.e., at least a 10%, preferably 20%, improvement in the parameter of interest with reference to the conventional measurement of such parameter, is contemplated. For example, if bioproduction of a cell is abnormally low or high, at least a 10% increase or decrease by mass, respectively, of the product of interest over a comparable time period is contemplated. Thus, if a given leukocyte biomass produces 10 ng of IgG over a one-hour period under normal in vitro conditions, the same biomass will produce at least 11 ng IgG over the same time period under the same culture conditions on exposure to the modulators of the invention. By the same token, the growth rate of a biomass of malignant cells exhibiting an abnormally high growth rate is decreased by at least about 10% on exposure to the modulators of the invention. Similarly, in vivo, rectification of abnormal cell differentiative activity of at least about 10% is established by comparing cell or organ activity before and after exposure to the modulators of the invention according to standard measuring techniques, such as blood determinations for the product of interest, NMR or CAT scans for evaluation of cellular activity, weight assessments for determination of cell growth, and a variety of other biotechnical diagnostic procedures wellknown in the art.

For use of differentiators according to the invention to diversify or expand cell differentiative activity, a similar, about 10%, preferably about 20% increase, in cell differentiative activity, based on conventional measurements of the parameter of interest is contemplated. For example, exposure of stimulated murine splenocytes to the differentiators promotes the production of antibody, with at least la 10% increase in antibody diversity with respect to affinity, avidity, and/or specificity of the antibody pool produced. With respect to modification of cell structure, at least about a 10% change in cell structure, particularly cell component biochemical characteristics, chemical characteristics, or stereochemical arrangement of cell components is contemplated. For example, a change in the oligosaccharide content of cell-surface membranes, as measured, for example, by lectin binding, of at least about 10%, preferably at least about 20%, is contemplated. As hereinbefore described, oligosaccharide cell-surface membrane characteristics have been correlated with cell growth patterns, and a modulation of abnormal cell-surface membrane oligosaccharide content with the differentiators of the invention to provide at least about 10% reduction in abnormally high cell reproduction rates, or at least about a 10% increase in abnormally low cell reproduction rates, as observed in senescent cells, for example, is within the scope of the invention. In this instance, for example, improvements in cell differentiative activity are measurable in vitro by either a change in the rate of lectin binding, reflecting a change in oligosaccharide cell-surface membrane characteristics, or by a direct measurement of cell reproduction activity, typically determined by change in generation time (Tg) as described, e.g., in the Examples.
E. Administration of Compounds Dosage of compounds of the Formula I according to the invention appear to be critical, i.e., dosages in excess of the therapeutic dosage range are typically ineffective to increase response and may actually, for example, stimulate tumor growth, while dosages below the range are substantially ineffective, for example, in inhibiting tumor burden. The differentiators of the invention are generally effective in dosage units in mammals of from about 100 ng/kg to about 100 µg/kg, administered, for example, from about once a day to once a week. The differentiators have no observed toxic side effects at therapeutic dosage levels. Any conventional route of administration is employed, such as i.v., i.p., or oral administration, employing conventional pharmaceutically-acceptable carriers such as physiological saline, and optional adjuvants. For humans, i.v., i.p., or sub-cutaneous injection of the differentiators agent at therapeutic dosage levels as anti-tumor agents on a regimen of at least alternate days until tumor response is noted, preferably by non-invasive diagnostic techniques such as nuclear magnetic resonance imaging (NMRI), is recommended. Initial positive tumor response (such as tumor deformity or presence of tumor-associated edema) is contemplated as observable as early as about two weeks from the start of the therapeutic regimen. After substantial tumor response has been achieved, dosage frequency may be decreased to, for example, a weekly basis, until the tumor has been conquered.

In an exemplary procedure, administration of a therapeutic dosage of cytostatic compound is begun on a human tumor host on Monday of week 1. 100 ng/kg in physiological saline is administered i.v., or i.p. Monday, Wednesday, and Friday of week 1; this procedure is repeated on continuous weeks 2, 3, 4, and following weeks with NMR monitoring on a weekly basis until the desired reduction in tumor burden is achieved. While the regimen may be continued thereafter, experimental evidence indicates that tumor rebound after treatment is not significantly incident to the therapeutic process of the invention.

EXAMPLE I

In the following Examples, the compounds employed are compounds of the formulas IIa–IIc, wherein A is

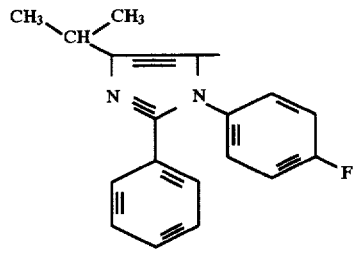

herein designated as IIa', IIb', and IIc'. Comparison compound IId' is

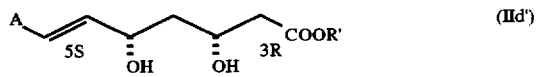

(IId')

wherein A and R' are the same as in compounds IIa'–IIc'. "Compound" IIe' is a racemic mixture of compounds IIb' and IIc'.
Compound TF-004 is:

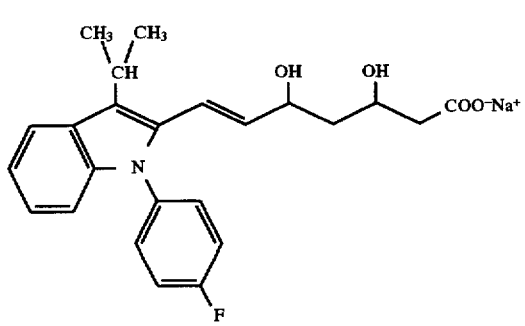

Compound TF-002 is:

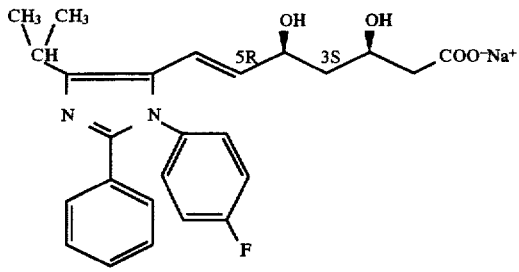

EXAMPLE II

Immunological Activity In Vitro

A. Immune Response of Human Peripheral Blood Leukocytes (HPBL)

Human peripheral blood leukocytes were cultured in a standard tissue culture medium. Aliquots of these cultured cells (1,000,000 cells/ml medium) were cultured for 6 hours, and the specified amount specified amount of Formula II compound was added; the cells were then cultured for an additional 90 hours. Sheep red blood cells (SPBC) conditioned with class-specific (IgG) goat anti-human antiserum (1:400) for 2 hours; then guinea pig complement (2%) for 2 hours were conjugated to Protein A as described in detail in *Radioimaging and Radioimmunotherapy*, Eds. S. W. Burchiel and B. A. Rhodes, Elsevier Science Publishing; New York, 1983, pp. 125–127, incorporated herein by reference.

Results of this study for compounds of the Formula IIa'–IIe' are given in Table I below:

TABLE I

| Compound | Inhibitory Concentration[1] | Stimulation of IgG Production Concentration/Percent | $IC2_{50}$ | Proliferation[3] |
|---|---|---|---|---|
| IIa' | none found | 200 pM/1700 | 3.150 | 0.98 |
| IIb' | none found | 200 pM/1700 | 1.350 | 1.0 |
| IIc' | none found | 100 pM/6200 | 0.022 | 1.2 |
| IId' (comparison) | 1.2 µM | 100 nM/320 | 0.002 | 0.66 |
| IIe' | 1.2 µM | 1 & 100 nM/1990 | 0.003 | 0.85 |

[1] Concentration inhibiting nonspecific IgG production below normal production.
[2] Concentration (µM) for 50% inhibition of rat liver HMG-CoA reductase activity; data obtained according to Example IA.
[3] Measured by ($^3$H) thymidine incorporation into DNA.

As is apparent from the above results, each of the cytostatic compounds of the invention (IIa', IIb', IIc', IIe') stimulated IgG production. Compound IIe' suppressed IgG production at a concentration of 1.2 µM, and exhibited substantially no significant enhancement (less than 350%) at lower concentrations (100 pM). In contrast, compounds IIa' and IIb' each stimulated IgG production 1700% at 200 pM concentration, and compound IIc' stimulated IgG production 6200% at 100 pM. There was no apparent correlation between induction of immunological activity and inhibition of HMG-CoA reductase activity ($IC_{50}$).

It is contemplated that therapeutic dosages of compounds which inhibit IgG production at relatively high concentrations in vitro according to the present Example (e.g., IIe') should be carefully controlled in vivo to avoid this effect.

EXAMPLE III

Immune Response In Vivo

1. Humoral Immunity

Tumor-specific Antibody Production

Titer of CG-specific antibody was compared to control [no administration of compound IIa' and no implantation of CG (canine glioma) cells]. As is apparent in the results described below in Table II, after administration of compound IIa' in the absence of antigen, titers of antibody increased over the control antibody titer significantly. Following implantation of the CG tumor cells, CG-specific antibody (IgG) production increased significantly (Table II). This increase in titer continued with time until tumor regression was noted by independent measurement (NMR evaluation, below). At this point the CG-specific antibody rapidly (within a few days) reverted to baseline control levels (Table II).

The results demonstrate an in vivo temporal and quantitative correlation between enunciation and degree of tumor-specific immunoglobulin response and the progression and ultimate regression of the tumor. The results are particularly striking as the experimental tumor (brain glioma) is generally considered to enjoy a privileged position beyond the blood/brain barrier, substantially beyond the reach of the humoral immune system. Experimental protocols are described in detail below (FIGS. 7–9, Example VII).

TABLE II

PRODUCTION OF SPECIFIC ANTI-CG IgG ANTIBODIES IN A DOG TREATED WITH COMPOUND IIC'

| TREATMENT | CG IMPLANTATION | IC-50% TITER (ANTI-CG) |
|---|---|---|
| NO | NO | BASELINE VALUES |
| YES (2 MONTHS) | NO | 0.0156 |
| YES (2 MONTHS) | YES (10–15 DAYS) | 0.001 |
| YES (2+ MONTHS) | TUMOR REGRESSED | BASELINE VALUES |

2. Cellular Immunity

Cellular immune response reflected the results reported in III, 1 above. As set forth in Table III, below, chromium-release cell-mediated lympholysis (CML) of the canines employed in Example III, 1 above, demonstrate a comparable cellular immunity to the humoral immunity therein set forth. After 14 days of administration (I.P. injection in physiological saline, M, W, F) of compound IIa', only baseline levels of CG-specific CML were present. After an additional 2 months of administration of compound IIa', there was a significant increase in CML. This also is in the absence of CG antigen exposure. Then, after only a few days of exposure to the CG tumor implant, there was a large increase in the CML reactivity (see Table III). Then after 5 weeks, at which time the tumor had totally regressed by independent measurement, the CML reactivity again returned to baseline. Thus both cellular and humoral immunity appear to be modulatable in the absence of antigen by the compounds of the instant invention.

17

TABLE III

CELLULAR CYTOTOXICITY VS CG TUMOR IN A DOG TREATED WITH COMPOUND IIc'

| DATE OF ASSAY | Y = "M" X + B (LINEAR REGRESSION OF TOXICITY) |
|---|---|
| December 14, 1987 | Y = 0.05 X + B |
| February 9, 1988 | Y = 0.35 X + B |
| February 17, 1988 | Y = 0.75 X + B |
| March 31, 1988 | Y = 0.05 X + B |

EXAMPLE IV

Inhibition of Tumor Cells In Vitro

Canine glioma cells were cultured as below with varying concentrations of compound IIe' and compactin (U.S. Pat. No. 3,983,140) for different times of exposure. Cytotoxicity was determined as a function of simple survival ($T_{50\%}$), adherence ($ADH_{50\%}$) and thymidine incorporation ($I_{50\%}$) of the cells. Results are summarized in Tables IV and V, below:

TABLE IV

CANINE GLIOMA CELLS: THE 50% TOXICITY AND INHIBITION OF ADHERENCE LEVELS

| DRUG | TIME OF EXPOSURE (h) | T 50% (nM) | $ADH_{50\%}$ (nM) |
|---|---|---|---|
| IIe' | 24 | 750 | 75 |
|  | 72 | 800 | 70 |
|  | 96 | 900 | 75 |
| COMPACTIN | 24 | 500 | 50 |
|  | 72 | 200 | 75 |
|  | 96 | 350 | 75 |

Estimates of the 50% inhibitory concentrations of the various drugs tested on simple survival ($T_{50\%}$) and adherence ($ADH_{50\%}$) for canine glioma cells.

TABLE V

CANINE GLIOMA CELLS: THE 50% INHIBITION OF THYMIDINE INCORPORATION

| DRUG | TIME OF EXPOSURE (h) | $I_{50\%}$ (nM) |
|---|---|---|
| IIe' | 24 | 50 |
|  | 48 | 75 |
|  | 72 | 80 |
|  | 96 | 50 |
| COMPACTIN | 24 | 100 |
|  | 48 | 75 |
|  | 72 | 30 |
|  | 96 | 50 |

Estimates of the $I_{50\%}$ of the various drugs tested on thymidine incorporation of canine glioma cells in culture.

As is apparent from Table IV, compound IIe' was cytotoxic to tumor cells in the range of 700 to 900 nM.

In the same concentration range, compound IIe' significantly inhibited thymidine incorporation into DNA ($I_{50\%}$ 50–80 nM, Table V).

Compound IIe' is a potent inhibitor of HMG-CoA reductase, having an $IC_{50}$ of 3 nM and $ED_{50}$ of 25 µg/kg (Example I).

EXAMPLE V

Effect on Tumor Cell Generation Time

A. Canine Glioma Cells

Canine glioma cells were cultured as described in Example IV and exposed to either a 10 nM concentration of compound IIe' and DMSO (dimethylsulfoxide), or DMSO alone as control. The cells were harvested every 72 hours after the controls had reached 85% confluency. Generation time (Tg) was determined as the number of hours required for the cell population to double. Results are summarized in Table VI.

TABLE VI

THE EFFECT OF COMPOUND IIe' ON CANINE GLIOMA GENERATION TIMES

| CONDITIONS | EXPOSURE TIME (h) | Tg (h) | % CHANGE |
|---|---|---|---|
| 10 Nm (Experimental) | 72 | 25.3 | 136 |
| 0 (Control) | 72 | 18.6 + 4.2 |  |
| 10 nM | 72 × 2 | 24.0 | 129 |
| 10 nM | 72 × 3 | 33.4 | 180 |
| 10 nM | 72 × 4 | 28.9 | 155 |

Mean of triplicate determinations. Canine glioma cells were grown under conditions to promote exponential growth characteristics; $2\times10^5$ cells in a T-25 flask. The cells were harvested every 72 hours after the controls had reached approximately 85% confluency. The drug was added at the initiation of culture in DMSO, the control cultures had just DMSO. The drug concentration was adjusted with DMSO so that the final concentration of DMSO was always 0.5%.

As is seen from the Table, after three passages there was an increase in the generation time from 18.6 h (control tumor cells) to 33.4 h (experimental) for three passages. This represents a 1.8-fold slowing of the growth rate. In addition, tumor cells treated with compound IIe' showed evidence of contact inhibition as the cells approached confluency, a phenomenon seen with nontransformed cells but not seen in transformed cell lines. (Control canine glioma cells continue to grow rapidly when reaching confluency and do not exhibit appropriate contact inhibition).

B. Human Colon Carcinoma Cells

The procedure of Example VA, above, was repeated except a human colon carcinoma cell line (LS-174) was used instead of the canine glioma cell line. Results are summarized in Table VII below.

TABLE VII

THE EFFECT OF COMPOUND IIe' ON LS-174 GENERATION TIMES

| CONDITIONS | EXPOSURE TIME (h) | Tg (h) | % CHANGE |
|---|---|---|---|
| 10 Nm (Experimental) | 72 | 84.9 | 320 |
| 0 (Control) | 72 | 26.5 |  |
| 10 nM | 72 × 2 | 106.2 | 400 |
| 10 nM | 72 × 3 | 110.3 | 416 |
| 10 nM | 72 × 4 | 109.6 | 414 |

Mean of triplicate determinations. LS-174 cells (human colon carcinoma) were grown under conditions to promote exponential growth characteristics; $2\times10^5$ cells in a T-25 flask. The cells were harvested every 72 hours after the controls had reached approximately 85% confluency. The drug was added at the initiation of culture in DMSO, the control cultures had just DMSO. The drug concentration was adjusted with DMSO so that the final concentration of DMSO was always 0.5%.

The results in slowing of the generation time were similar to those set forth in Table VI, but were more striking. Untreated control tumor cells had a generation time of 26.5 h. After three passages in the presence of Compound IIe', the generation time was prolonged by 4.16-fold to 110.3 h. When the drug was withdrawn (two passages), the generation time returned to control levels (data not shown).

EXAMPLE VI

In Vivo Tumor Inhibition: Nude Rat Model
Canine Glioma

Fifty four Nude Rats (Harlan) were injected in the right flank with $5 \times 10^6$ canine glioma cells. Animals at the time of injection were between 52 and 63 days old and weighed approximately 200 g. The rats were divided into 7 groups, each group having a total number of 7 rats except for the control group, which totalled 12 animals. Compound IIc' was administered to the experimental animals at one of the following dose for each experimental group: 100 µg/kg, 10 µg/kg, 1 µg/kg, 0.1 µg/kg, 0.01 µg/kg and 0.001 µg/kg (phosphate buffer saline, M, W, F, I.P.). The control animals were injected with PBS (phosphate buffered saline) only. The volume of each injection was 100 µl. The injections of drug were simultaneously begun with injection of tumor cells. The animals were injected with the appropriate dosage of drug (1 ng/kg to 100 ng/kg) by I.P. injection and tumor length, width and depth were measured using caliphers each Monday, Wednesday and Friday (M, W, F) morning for approximately 9 weeks. Each point on the graphs represents the total of all rats for each group. Where the points show a break ("), regression did not occur and the rats were sacrificed. The data were normalized for the greater number of control animals by multiplying the total tumor volume for the control animals by $7/12$.

Results are summarized in FIGS. 1–6.

Figure 3:
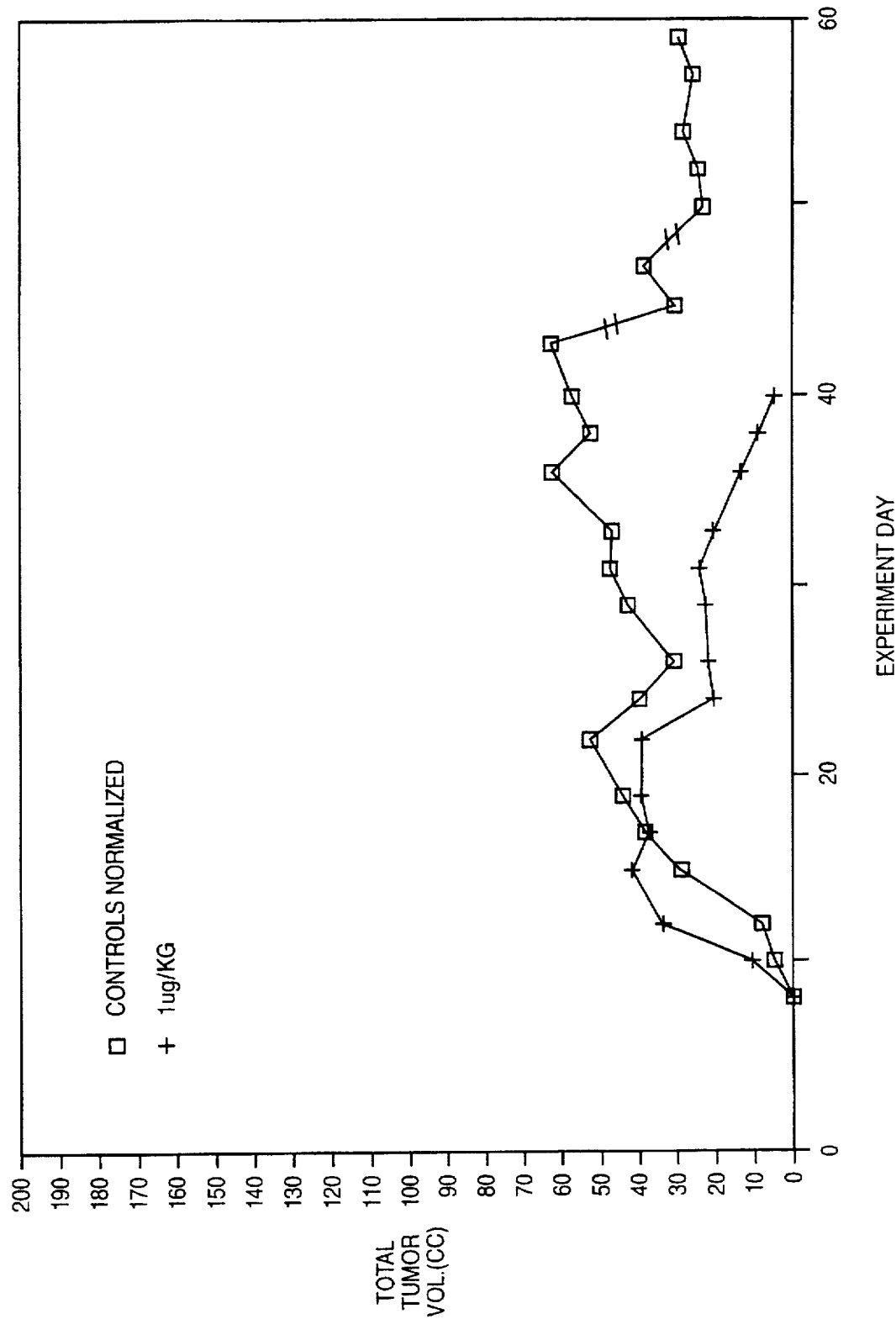
Figure 4:
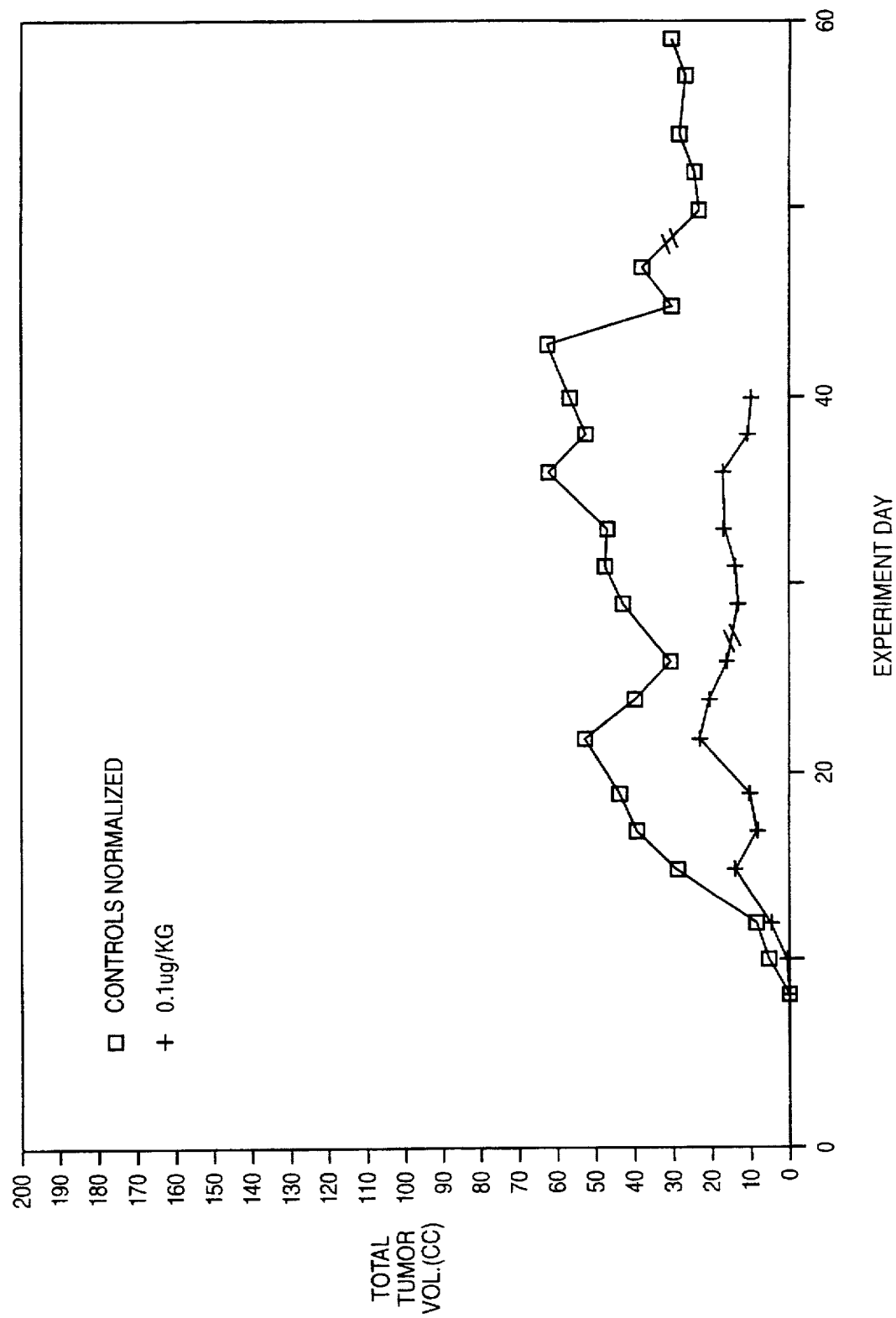
Figure 5:
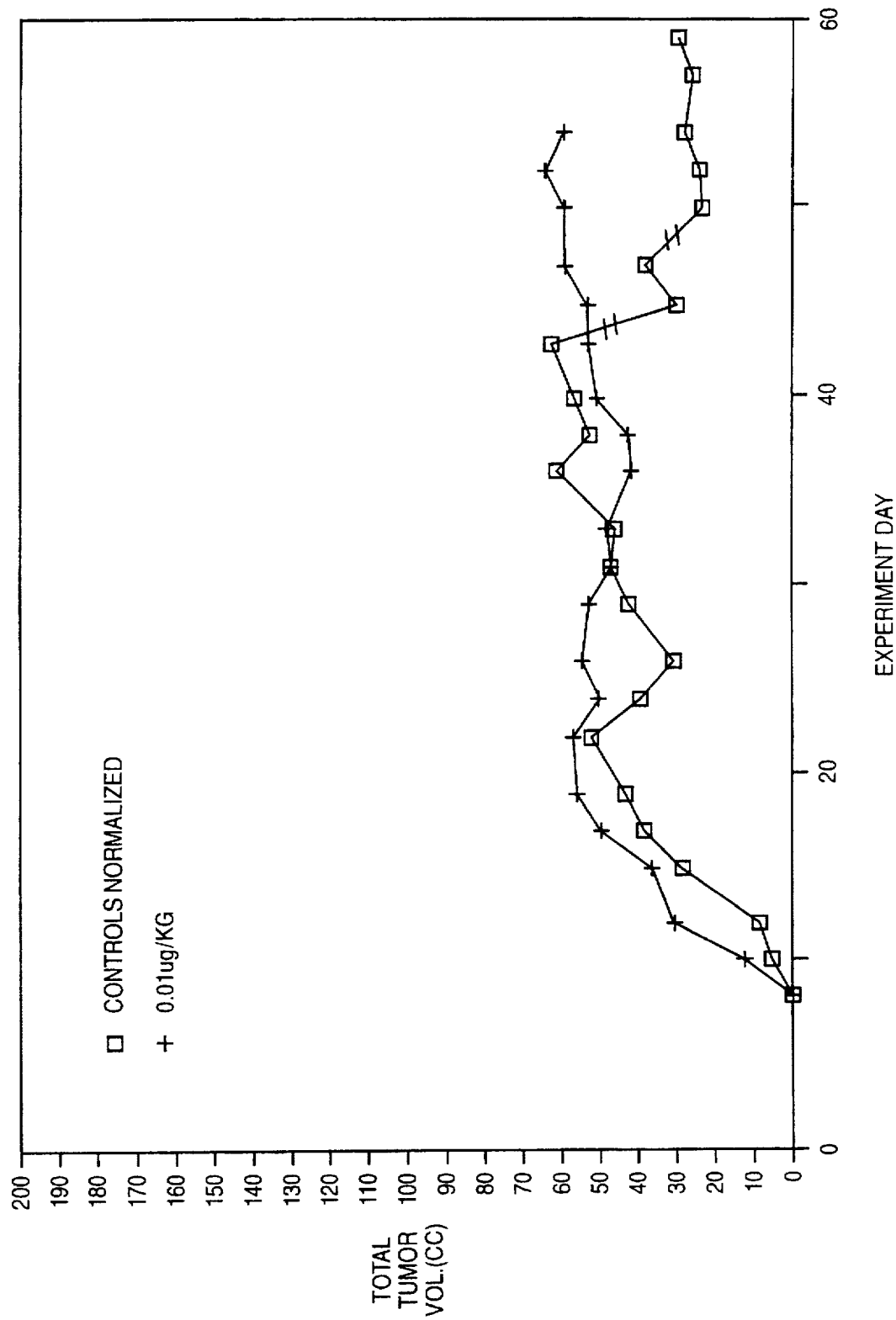
Figure 6:
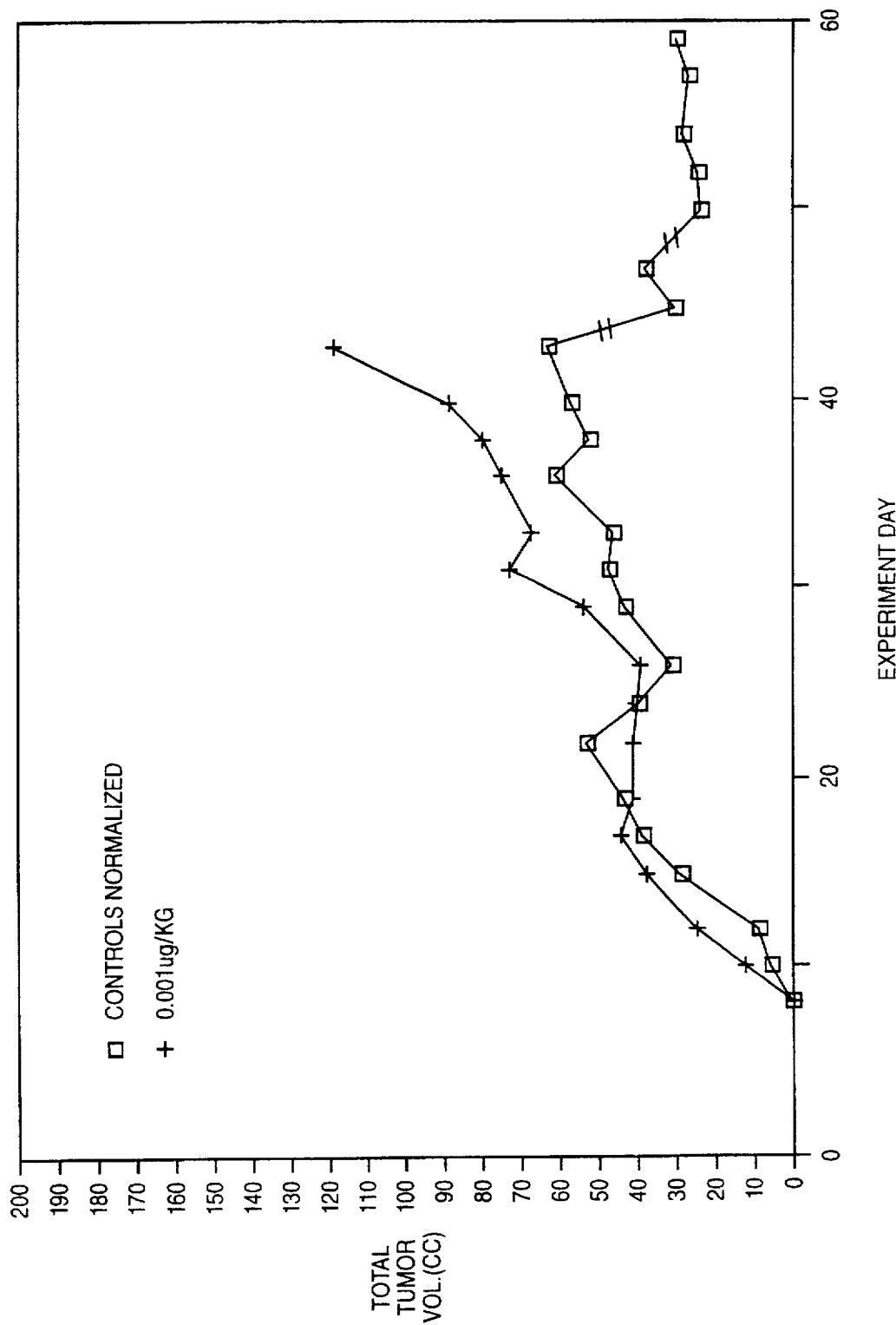

The Harlan nude rat model employed has partially compromised immunological competency. The experimental compound IIc' is a potent immune stimulant (see Examples, above). The most effective dosage for inhibition of canine glioma cells in this model was 100 ng/kg (FIG. 3). Little or no cytostatic activity was exhibited at the higher doses employed (10 and 100 µg/kg) or at the lowest dose of 1 ng/kg. The optimal dosage for cytostatic activity in vivo closely correlates with the optimal dosage for immune stimulation in vitro (example IIA, HPBL assay). The optimal dose in vivo (100 ng/kg, equivalent to 250 pM with uniform distribution) compares to the optimal dose in vitro, 100 pM.

Similar anti-tumor activity has been observed with Compounds IIa', IIe' and TF004.

EXAMPLE VII

In Vivo Tumor Inhibition: Canine Model

Canine glioma was implanted surgically into the brains of four outbred dogs ($2 \times 10^6$ cells). This procedure normally causes death by tumor growth in 14–28 days.

Simultaneous with implantation, the dogs were each placed on a regimen of compounds according to the invention. Compounds IIa', Ie' and TF004 in various dosages were administered on alternate days (M, W, F) by I.P. injection in phosphate buffered saline.

Tumor progress was assessed at weekly intervals by NMR, employing GdDPTA as imaging agent. This method illuminates vascularization at the surface of the tumor, and provides images which correlate well with neuropathological observations. The compounds were found to have a direct, early effect on the tumor, evidenced in this NMR procedure as a substantial edema in the vicinity of the tumor.

The experiments and results are summarized as follows:

FIG. 7 shows the rapid and progressive growth of the canine glioma tumor after implantation in the left frontal lobe of three dogs. These animals were sacrificed at 12 to 19 days because they were showing significant neurological deficit. This tumor would certainly kill the dogs by 14 to 28 days.

FIG. 8 shows a dog with an implanted canine glioma in the left frontal lobe of the brain. This animal was pre-treated with TF-002. After implantation, treatment with TF-002 [10 µg/kg, I.P., on alternate days (M, W, F)] was continued. A small tumor appeared on Day 12. It regressed by Day 19. Later studies (data not shown) showed this animal to be free of tumor.

FIG. 9 shows two dogs treated with TF-004. The line shown by squares (□—□) represents tumor size in the dog where treatment was begun on the same day (1 µg/kg I.P. on alternate days, i.e., M, W, F) as tumor implantation. A tumor was visible on Days 8 and 12. Substantial regression had occurred by Day 15 and complete regression occurred by Day 21. Another dog (x—x) received a canine glioma in the left frontal lobe by surgical implantation. A tumor was visible at Day 10. Treatment with TF-004 was begun on Day 11. Substantial regression was observed by Day 21 and complete regression was observed by Day 30.

CANINE GLIOMA MODEL SYNOPSIS

Complete tumor regression was observed in all four animals. The most marked result was observed in the canine treated with TF-004, at a dosage rate of 1 µg/kg, i.p. Treatment of this dog was begun on Day 11 after implantation, when a large brain tumor had been established. Complete regression of the tumor occurred by Day 30 after implantation.

It is postulated that the modulators described herein influence a sufficiently primitive biochemical control process which affects the regulation of cell differentiation at a sufficiently basic level, to have a substantially universal function as a modulator of cell activity to promote normal cell differentiative function over a broad spectrum of cells. It is specifically contemplated that the modulators of the invention function to rectify abnormal production of a variety of protein, glycoprotein, carbohydrate and fat cell products, as well as enzymes; hormones, such as somatostatin, MSH (melanocyte-stimulating hormone), and pituitary hormones; immunoproducts such as lymphokines, globulins and antigens; cholesterol; to reassert normal cell function, such as the normal function of liver cells; to correct cell deficiencies such as immunodeficiencies, glandular deficiencies such as hypothalmia, and metabolic deficiencies; to restore normal growth patterns to cells exhibiting decelerated growth rates such as senescent cells or accelerated growth rates such as malignant cells; to modulate aberrant cell structures to approach those of normal cells; to stimulate progenitor and/or precursor cells into full production of mature cells; and, further, to diversify and/or expand existing cell function within the genetic capabilities of the cell, such as to increase the immunoresponse of splenocytes to antigenic stimulus with respect to both the diversity and amount of antibodies produced.

The differentiators exert biochemical control over cell differentiation processes, intervening at a very early point in cellular differentiative pathways to promote cell autoregulation of differentiative function. It is accordingly believed that the modulators described herein comprise molecules which, with respect to both biologically-active functional moieties and with respect to the presentation of the biologically-active functional groups to the cell (i.e., the stereochemistry of the molecule), function to counteract cellular imbalances resulting in abnormal differentiative function over a broad spectrum of cells and differentiative activity. Thus, in contrast to known prior art differentiators which tend to be relatively specific in effect, with respect to either particular cells or particular differentiative activity, the modulators of the present invention are effective in restoring normal differentiative function to chemically imbalanced cells of plants, animals (especially mammals including humans), microorganisms, viruses, and insects. Further, the modulators of the invention function to increase diversity of differentiative function within the genetic potential of the cell.

Clinical Applications

The compounds described in the present invention induce or enhance cellular differentiation, i.e., they maximize and/or normalize cellular phenotypic expression. Therefore, they will be of therapeutic benefit in diseases characterized by either (1) diminished cellular function or (2) aberrant cellular function. Examples of the first category include acquired immune deficiency syndrome (AIDS) and hypogammaglobulinemia. Another example of the first category is the treatment of infectious diseases caused by pathogens of bacterial, fungal, rickettsial, viral or parasitic origin. The compounds of the invention maximize the function of immunocytes by maximizing the phenotypic expression of these cells. Therefore, immunological recognition and elimination of these pathogens from the body are facilitated by treatment using the compounds described in the invention. Patients with atherosclerosis benefit by treatment with the compounds of this invention, since phenotypic expression (differentiation) of liver cells (hepatocytes) are induced and enhanced. This leads to increased levels of the LDL receptor on the surface of hepatocytes and this facilitates the removal of cholesterol from the body.

Diseases of the second category, i.e., aberrant cellular function, include cancer, as well as autoimmune diseases such as diabetes, multiple sclerosis, lupus erythematosus and rheumatoid arthritis.

What is claimed is:

1. A method for treating a glioma or colon carcinoma in a mammal comprising administering to the mammal a therapeutically effective amount of a compound of the formula:

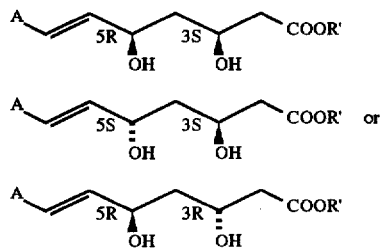

wherein A is

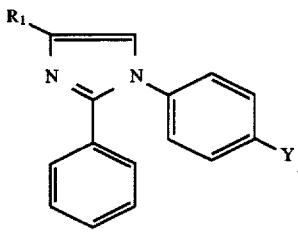

wherein $R_1$ is $C_{1-6}$ alkyl,

Y is fluoro-, chloro- or bromo- and wherein R' is hydrogen, a physiologically-acceptable cation or cation complex or a physiologically acceptable ester group.

2. A method for treating a glioma or colon carcinoma in a mammal comprising administering to the mammal a therapeutically effective amount of a compound of the formula:

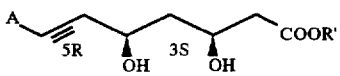

wherein A is

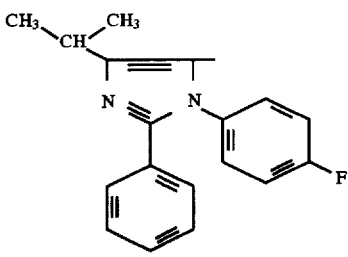

and wherein R' is hydrogen, a physiologically-acceptable cation or cation complex or a physiologically acceptable ester group.

3. A method for treating a glioma or colon carcinoma in a mammal comprising administering to the mammal a therapeutically effective amount of a compound of the formula:

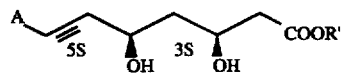

wherein A is:

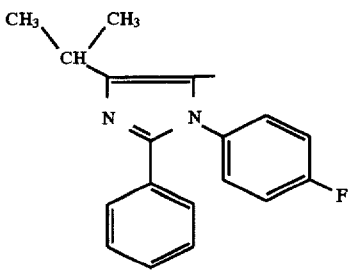

and wherein R' is hydrogen, a physiologically-acceptable cation or cation complex or a physiologically acceptable ester group.

4. A method for treating a glioma or colon carcinoma in a mammal comprising administering to the mammal a therapeutically effective amount of a compound of the formula:

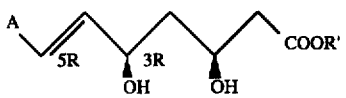

wherein A is:

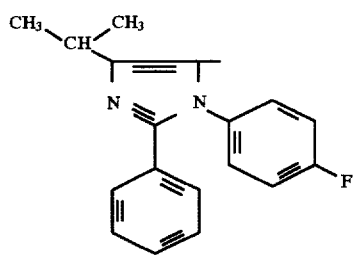

and wherein R' is hydrogen, a physiologically-acceptable cation or cation complex or a physiologically acceptable ester group.

5. A method for treating a glioma in a mammal comprising administering to the mammal a therapeutically effective amount of a compound of the formula:

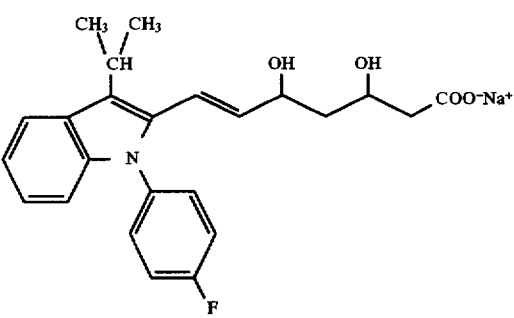

* * * * *

UNITED STATES PATENT AND TRADEMARK OFFICE
CERTIFICATE OF CORRECTION

PATENT NO. : 5,783,594
DATED : July 21, 1998
INVENTOR(S): Scallen et al.

It is certified that error appears in the above-identified patent and that said Letters Patent is hereby corrected as shown below:

Column 8, line 57, change

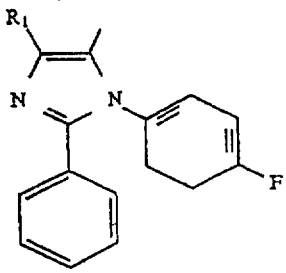

to

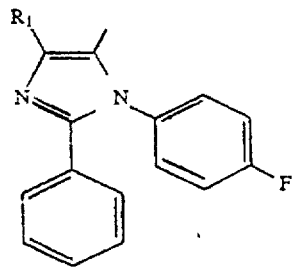

UNITED STATES PATENT AND TRADEMARK OFFICE
CERTIFICATE OF CORRECTION

Page 2 of 18

PATENT NO. : 5,783,594

DATED : July, 21, 1998

INVENTOR(S): Scallen et al.

It is certified that error appears in the above-identified patent and that said Letters Patent is hereby corrected as shown below:

Column 9, line 2, change

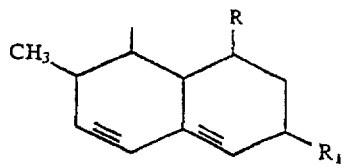

to

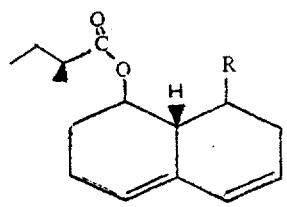

UNITED STATES PATENT AND TRADEMARK OFFICE
CERTIFICATE OF CORRECTION

Page 3 of 18

PATENT NO. : 5,783,594

DATED : July 21, 1998

INVENTOR(S): Scallen et al.

It is certified that error appears in the above-identified patent and that said Letters Patent is hereby corrected as shown below:

Column 9, line 14, change

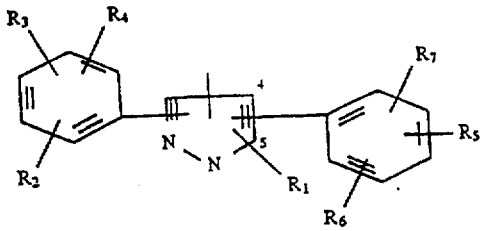

to

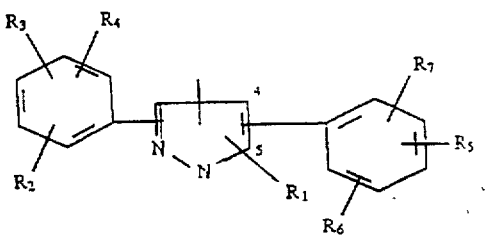

UNITED STATES PATENT AND TRADEMARK OFFICE
CERTIFICATE OF CORRECTION

PATENT NO. : 5,783,594

DATED : July 21, 1998

INVENTOR(S): Scallen et al.

It is certified that error appears in the above-identified patent and that said Letters Patent is hereby corrected as shown below:

Column 9, line 46, change

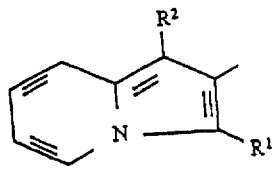

to

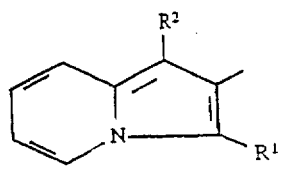

UNITED STATES PATENT AND TRADEMARK OFFICE
CERTIFICATE OF CORRECTION

PATENT NO. : 5,783,594

DATED : July 21, 1998

INVENTOR(S): Scallen et al.

It is certified that error appears in the above-identified patent and that said Letters Patent is hereby corrected as shown below:

Column 10, line 2, change

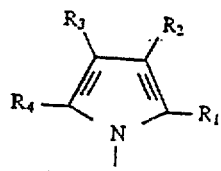

to

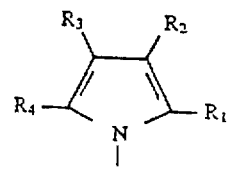

UNITED STATES PATENT AND TRADEMARK OFFICE
CERTIFICATE OF CORRECTION

Page 6 of 18

PATENT NO. : 5,783,594
DATED : July 21, 1998
INVENTOR(S): Scallen et al.

It is certified that error appears in the above-identified patent and that said Letters Patent is hereby corrected as shown below:

Column 10, line 15, change

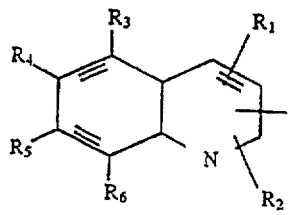

to

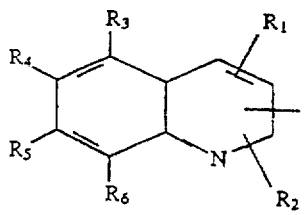

UNITED STATES PATENT AND TRADEMARK OFFICE
CERTIFICATE OF CORRECTION

PATENT NO. : 5,783,594

DATED : July, 21, 1998

INVENTOR(S): Scallen et al.

It is certified that error appears in the above-identified patent and that said Letters Patent is hereby corrected as shown below:

Column 10, line 27, change

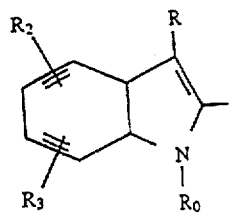

to

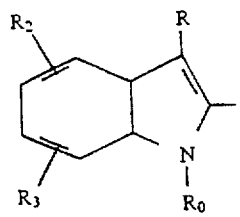

UNITED STATES PATENT AND TRADEMARK OFFICE
CERTIFICATE OF CORRECTION

PATENT NO. : 5,783,594
DATED : July 21, 1998
INVENTOR(S): Scallen et al.

It is certified that error appears in the above-identified patent and that said Letters Patent is hereby corrected as shown below:

Column 10, line 40, change

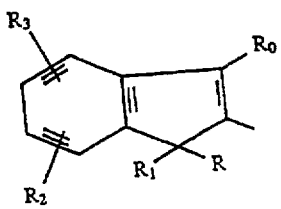

to

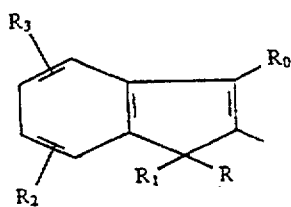

UNITED STATES PATENT AND TRADEMARK OFFICE
CERTIFICATE OF CORRECTION

PATENT NO. : 5,783,594
DATED : July 21, 1998
INVENTOR(S): Scallen et al.

It is certified that error appears in the above-identified patent and that said Letters Patent is hereby corrected as shown below:

Column 10, line 58, change

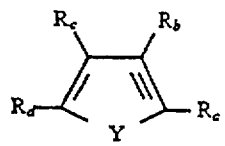

to

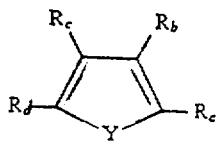

UNITED STATES PATENT AND TRADEMARK OFFICE
CERTIFICATE OF CORRECTION

PATENT NO. : 5,783,594

DATED : July 21, 1998

INVENTOR(S): Scallen et al.

It is certified that error appears in the above-identified patent and that said Letters Patent is hereby corrected as shown below:

Column 11, line 13, change

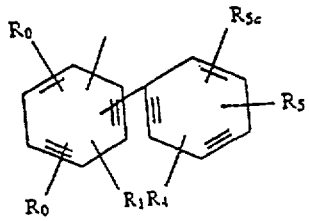

to

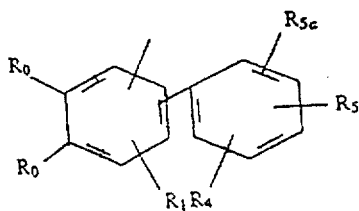

UNITED STATES PATENT AND TRADEMARK OFFICE
CERTIFICATE OF CORRECTION

PATENT NO. : 5,783,594

DATED : July 21, 1998

INVENTOR(S): Scallen et al.

It is certified that error appears in the above-identified patent and that said Letters Patent is hereby corrected as shown below:

Column 11, line 23, change

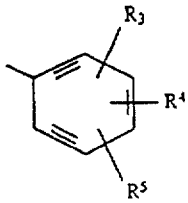

to

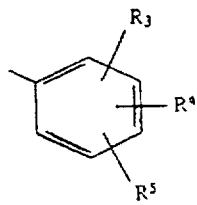

UNITED STATES PATENT AND TRADEMARK OFFICE
CERTIFICATE OF CORRECTION

Page 12 of 18

PATENT NO. : 5,783,594

DATED : July 21, 1998

INVENTOR(S): Scallen et al.

It is certified that error appears in the above-identified patent and that said Letters Patent is hereby corrected as shown below:

Column 11, line 34, change

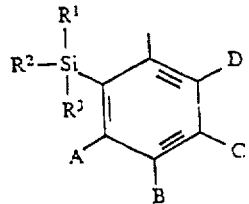

to

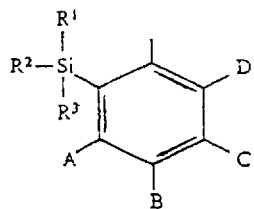

UNITED STATES PATENT AND TRADEMARK OFFICE
CERTIFICATE OF CORRECTION

Page 13 of 18

PATENT NO. : 5,783,594

DATED : July 21, 1998

INVENTOR(S): Scallen et al.

It is certified that error appears in the above-identified patent and that said Letters Patent is hereby corrected as shown below:

Column 14, line 31

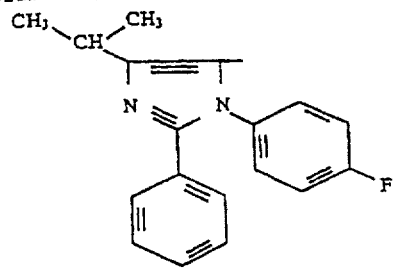

to

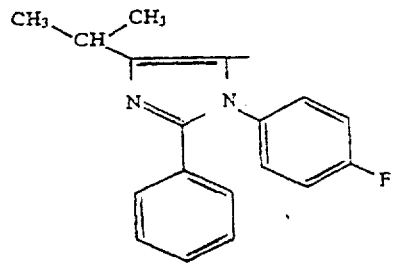

UNITED STATES PATENT AND TRADEMARK OFFICE
CERTIFICATE OF CORRECTION

PATENT NO. : 5,783,594

DATED : July 21, 1998

INVENTOR(S): Scallen et al.

It is certified that error appears in the above-identified patent and that said Letters Patent is hereby corrected as shown below:

Column 22, line 24, change

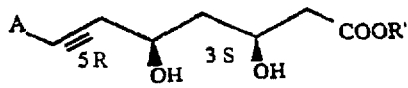

to

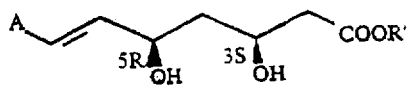

UNITED STATES PATENT AND TRADEMARK OFFICE
CERTIFICATE OF CORRECTION

Page 15 of 18

PATENT NO. : 5,783,594

DATED : July 21, 1998

INVENTOR(S): Scallen et al.

It is certified that error appears in the above-identified patent and that said Letters Patent is hereby corrected as shown below:

Column 22, line 29, change

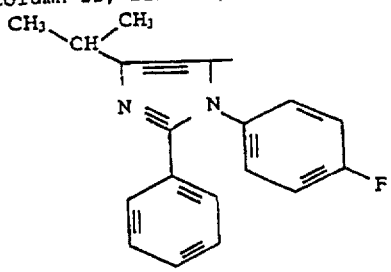

to

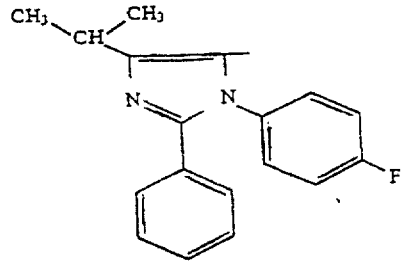

UNITED STATES PATENT AND TRADEMARK OFFICE
CERTIFICATE OF CORRECTION

PATENT NO. : 5,783,594
DATED : July 21, 1998
INVENTOR(S): Scallen et al.

It is certified that error appears in the above-identified patent and that said Letters Patent is hereby corrected as shown below:

Column 22, line 49, change

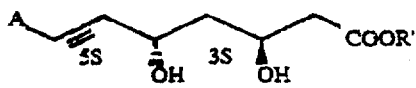

to

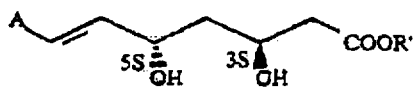

UNITED STATES PATENT AND TRADEMARK OFFICE
CERTIFICATE OF CORRECTION

PATENT NO. : 5,783,594
DATED : July 21, 1998
INVENTOR(S): Scallen et al.

It is certified that error appears in the above-identified patent and that said Letters Patent is hereby corrected as shown below:

Column 23, line 10, change

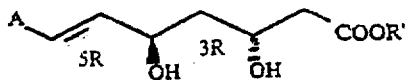

to

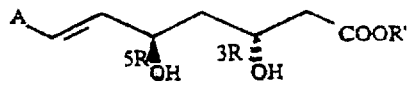

UNITED STATES PATENT AND TRADEMARK OFFICE
CERTIFICATE OF CORRECTION

PATENT NO. : 5,783,594

DATED : July 21, 1998

INVENTOR(S): Scallen et al.

It is certified that error appears in the above-identified patent and that said Letters Patent is hereby corrected as shown below:

Column 23, line 15, change

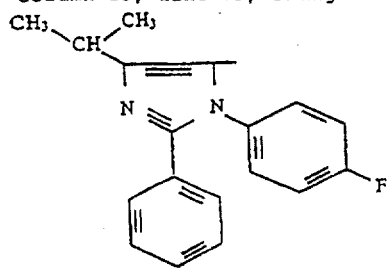

to

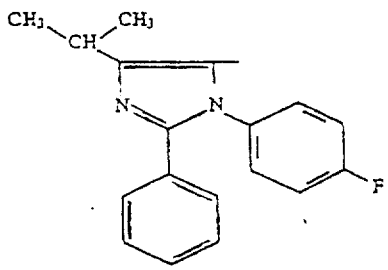

Signed and Sealed this

First Day of June, 1999

*Attest:*

Q. TODD DICKINSON

*Attesting Officer*   *Acting Commissioner of Patents and Trademarks*